US010245300B2

(12) United States Patent
Fasano et al.

(10) Patent No.: US 10,245,300 B2
(45) Date of Patent: Apr. 2, 2019

(54) GLUTEN-RELATED DISORDERS

(71) Applicant: H.J. Heinz Company Brands LLC, Pittsburgh, PA (US)

(72) Inventors: Francesca Romana Fasano, Sondrio (IT); Andrea Luigi Budelli, Gallarate (IT)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 605 days.

(21) Appl. No.: 14/408,108

(22) PCT Filed: Jun. 18, 2013

(86) PCT No.: PCT/US2013/046286
§ 371 (c)(1),
(2) Date: Dec. 15, 2014

(87) PCT Pub. No.: WO2013/192163
PCT Pub. Date: Dec. 27, 2013

(65) Prior Publication Data
US 2015/0174199 A1    Jun. 25, 2015

Related U.S. Application Data

(60) Provisional application No. 61/725,693, filed on Nov. 13, 2012, provisional application No. 61/661,105, filed on Jun. 18, 2012.

(51) Int. Cl.
| | |
|---|---|
| *A61K 38/16* | (2006.01) |
| *A61K 35/747* | (2015.01) |
| *A61K 31/045* | (2006.01) |
| *A61K 31/19* | (2006.01) |
| *A61K 31/198* | (2006.01) |
| *A61K 31/401* | (2006.01) |
| *A61K 31/4172* | (2006.01) |
| *A61K 31/708* | (2006.01) |
| *A61K 45/06* | (2006.01) |
| *C07K 14/335* | (2006.01) |
| *A23L 33/00* | (2016.01) |
| *A23L 33/135* | (2016.01) |

(52) U.S. Cl.
CPC .......... *A61K 38/164* (2013.01); *A23L 33/135* (2016.08); *A23L 33/30* (2016.08); *A61K 31/045* (2013.01); *A61K 31/19* (2013.01); *A61K 31/198* (2013.01); *A61K 31/401* (2013.01); *A61K 31/4172* (2013.01); *A61K 31/708* (2013.01); *A61K 35/747* (2013.01); *A61K 45/06* (2013.01); *C07K 14/335* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,599,504 B1 | 7/2003 | Wadstrom |
| 6,835,376 B1 | 12/2004 | Neeser |
| 9,980,991 B2 | 5/2018 | Fasano |
| 1,003,929 A1 | 8/2018 | Budelli |
| 2009/0186142 A1 | 7/2009 | Tatewaki et al. |
| 2010/0196341 A1 | 8/2010 | Wei |
| 2011/0028434 A1 | 2/2011 | Destaillats |
| 2011/0064707 A1 | 3/2011 | Rochat |
| 2011/0293724 A1 | 12/2011 | Hausch |
| 2012/0014963 A1 | 1/2012 | Benyacoub |
| 2014/0377238 A1 | 12/2014 | Budelli |
| 2016/0113973 A1 | 4/2016 | Fasano |
| 2017/0202231 A1 | 7/2017 | Budelli |

FOREIGN PATENT DOCUMENTS

| | | |
|---|---|---|
| CN | 1350461 | 5/2002 |
| CN | 101451158 | 6/2009 |
| CN | 102021127 | 4/2011 |
| CN | 102046028 | 5/2011 |
| CN | 102065872 | 5/2011 |
| EP | 0130228 | 1/1985 |
| EP | 1364586 | 11/2003 |
| EP | 1565547 | 9/2012 |
| EP | 2510932 | 10/2012 |
| RU | 2134583 | 8/1999 |

(Continued)

OTHER PUBLICATIONS

Cagno et al. "Sourdough Bread Made from Wheat and Nontoxic Flours and Started with Selected Lactobacilli is Tolerated in Celiac Sprue Patients". Applied and Environmental Microbiology, Feb. 2004, vol. 70, No. 2, p. 1088-1096.*
Robert et al. "Biodiversity of lactic bacteria in French wheat sourdough as determined by molecular characterization using specie-specific PCR". International Journal of Food Microbiology. 2009, vol. 135, No. 1, pp. 53-59.*
Savijoki et al. Applied and Environmental Microbiology. 2000, vol. 66, No. 2, pp. 794-800.*
Adams, Clifford A. "The Probiotic Paradox: Live and Dead Cells Are Biological Response Modifiers." Nutrition Research Reviews, 2010, vol. 23, No. 1, pp. 37-46.
Agostoni, Carlo, et al., "Fermented Infant Formulae Without Live Bacteria." Journal of Pediatric Gastroenterology and Nutrition, 2007, vol. 44, pp. 392-397.

(Continued)

*Primary Examiner* — Vera Afremova
(74) *Attorney, Agent, or Firm* — Fitch, Even, Tabin & Flannery LLP

(57) ABSTRACT

The present invention features compositions and methods for treating gluten-related disorders. We describe compositions comprising one or more metabolites produced by *Lactobacillus paracasei* CBA L74, International Depository Accession Number LMG P-24778 that reduce cellular entry of gliadin peptides. The compositions may include a physiologically acceptable carrier, for example, a food product or a pharmaceutical carrier. The compositions can be administered to a subject having a gluten-related disorder, for example, celiac disease or gluten sensitivity.

31 Claims, 20 Drawing Sheets

(56) References Cited

FOREIGN PATENT DOCUMENTS

| RU | 2205871 | 6/2003 |
|---|---|---|
| RU | 2243779 | 1/2005 |
| RU | 2385730 | 7/2008 |
| WO | 1997049303 | 12/1997 |
| WO | 1999029833 | 6/1999 |
| WO | 2001097822 | 12/2001 |
| WO | 2002018542 | 3/2002 |
| WO | 2002053706 | 7/2002 |
| WO | 2007140622 | 12/2007 |
| WO | 2008003782 | 1/2008 |
| WO | 2761691 | 11/2010 |
| WO | 2011039328 | 4/2011 |
| WO | 2011-110884 | 9/2011 |
| WO | 2012059501 | 5/2012 |
| WO | 2012059502 | 5/2012 |
| WO | 2012062781 | 5/2012 |
| WO | 2012140031 | 10/2012 |
| WO | 2012/177556 | 12/2012 |
| WO | 2012-177556 | 12/2012 |
| WO | 2014183050 | 11/2014 |

OTHER PUBLICATIONS

Chapat, Ludivine, et al., "Lactobacillus casei Reduces CD8+ T Cell-Mediated Skin Inflammation." European Journal of Immunology, 2004, vol. 34, pp. 2520-2528.

Chinese Patent Application No. 201380032073.2, First Office Action dated Jan. 25, 2016, 15 pages (with English translation).

Elias, Peter M., ""Outside-to-Inside" (and Now Back to "Outside") Pathogenic Mechanisms in Atopic Dermatitis." Journal of Investigative Dermatology, May 2008, vol. 128, No. 5, pp. 1067-1070.

European Patent Application No. 13807318, Supplemental European Search Report, dated Dec. 11, 2015, 7 pages.

Indrio, Flavia, et al., "Effect of a Fermented Formula on Thymus Size and Stool pH in Healthy Term Infants." Pediatric Research, 2007, vol. 62, No. 1, pp. 98-100.

International Patent Application No. PCT/US2013/046286, International Preliminary Report on Patentability and Written Opinion, dated Dec. 23, 2014, 7 pages.

International Patent Application No. PCT/US2013/046286, International Search Report, dated Aug. 23, 2013, 5 pages.

Iversen, Carol, et al., "Cronobacter gen. nov., a new genus to accommodate the biogroups of Enterobacter sakazakii, and proposal of Cronobacter sakazakii gen. nov., Cronobacter malonaticus . . ." International Journal of Systematic and Evolutionary Microbiology, 2008, vol. 58, pp. 1442-1447.

Kalliomaki, Marko, el al., "Distinct Fattens of Neonatal Gut Microflora in Infants in Whom Atopy Was and Was Not Developing." Journal of Allergy and Clinical Immunology, Jan. 2001, vol. 107, No. 1, pp. 129-134.

Kirjavainen, P.V., et al., "Aberrant Composition of Gut Microbiota of Allergic Infants: A Target of Bifidobacterial Therapy at Weaning?" Gut, 2002, vol. 51, pp. 51-55.

Lee, Joohee, et al., "Meta-Analysis of Clinical Trials of Probiotics for Prevention and Treatment of Pediatric Atopic Dermatitis." Journal of Allergy and Clinical Immunology, Jan. 2008, vol. 121, No. 1, pp. 116-121.

Moroi, Miki, et al., "Beneficial Effect of a Diet Containing Heat-Killed Lactobacillus Paracasei K71 on Adult Type Atopic Dermatitis." Journal of Dermatology, 2011, vol. 38, pp. 131-139.

Wagner, R. Doug, et al., "Probiotic Effects of Feeding Heat-Killed Lactobacillus acidophilus and Lactobacillus casei to Candida albicans-Colonized Immunodeficient Mice." Journal of Food Protection, 2000, vol. 63, No. 5, pp. 638-644, Abstract only.

Winkler, Petra, et al., "Molecular and Cellular Basis of Microflora-Host Interactions." The Journal of Nutrition, 2007, vol. 137, pp. 756S-772S.

D'Arienzo, R., et al., "Distinct Immunomodulatory Properties of Lactobacillus Paracasei Strains." Journal of Applied Microbiology, 2011, vol. 111, pp. 1482-1491.

Grandy, Giuseppe, et al., "Probiotics in the Treatment of Acute Rotavirus Diarrohoea. A Randomized, Double-Blind, Controlled Trial Using Two Different Probiotic Preparations in Bolivian Children." BMC Infectious Diseases, 2010, vol. 10, pp. 1-7.

Gallo, Marianna. "Formulation of Functional Food Using Constituents Modified by Biochemical and Physical Processes," PhD Dissertation, Universita degli studi di Napoli, Department of Engineering Chemistry, 2009, pp. 1-132.

Sanz et al., "Unraveling the ties between celiac disease and intestinal microbiota", International Reviews of Immunology, vol. 30, No. 4, 2011, pp. 207-218.

Hir et al., "Gluten proteolysis as alternative therapy for celiac patients: A mini-review", African Journal of Biotechnology, vol. 11, No. 29, Apr. 10, 2012, pp. 7323-7330.

Angelis et al., "VSL# 3 probiotic preparation has the capacity to hydrolyze gliadin polypeptides responsible for celiac sprue probiotics and gluten intolerance", Biochimica et Biophysica Acta, vol. 1762, No. 1, 2006, pp. 80-93.

Arienzo et al., "Modulation of the immune response by probiotic strains in a mouse model of gluten sensitivity", Cytokine, vol. 48, No. 3, 2009, pp. 254-259.

Dong, Honglin, et al., "Comparative Effects of Six Probiotic Strains on Immune Function in vitro." British Journal of Nutrition, 2012, vol. 108, pp. 459-470.

Di Cagno, Raffaella, et al., "Use of Selected Sourdough Strains of Lactobacillus for Removing Gluten and Enhancing the Nutritional Properties of Gluten-Free Bread." Journal of Food Protection, vol. 71, No. 7, 2008, pp. 1491-1495.

Ortiz-Andrellucchi, Adriana, et al., "Immunomodulatory Effects of the Intake of Fermented Milk with Lactobacillus casei DN114001 in Lactating Mothers and Their Children." British Journal of Nutrition, 2008, vol. 100, pp. 834-845.

Rizzello, Carlo G. et al., "Highly Efficient Gluten Degradation by Lactobacilli and Fungal Proteases during Food Processing: New Perspectives for Celiac Disease." Applied and Environmental Microbiology, Jul. 2007, vol. 73, No. 14, pp. 4499-4507.

Kearney, N., et al., "Development of a Spray Dried Probiotic Yoghurt Containing Lactobacillus Paracasei NFBC 338." International Dairy Journal, 2009, vol. 19, pp. 684-689.

Bar, F., et al., "Cell-free Supernatants of *Escherichia coli* Nissle 1917 Modulate Human Colonic Motility: Evidence from an in Vitro Organ Bath Study." Neurogastroenterol Motil, 2009, vol. 21, pp. 559-566.

Chiang, Shen-Shih, et al., "Beneficial Effects of Lactobacillus paracasei subsp. paracasei NTU 101 and Its Fermented Products." Applied Microbiology Biotechnology, 2012, vol. 93, pp. 903-916.

Gardiner, Gillian E., et al., "A Spray-Dried Culture for Probiotic Cheddar Cheese Manufacture." International Dairy Journal, vol. 12, 2002, pp. 749-756.

Jimenez, Esther, et al., "Is meconium from healthy newborns actually sterile?" Research in Microbiology, vol. 159, 2008, pp. 187-193.

Kristo, E., et al., "Modelling of Rheological, Microbiological and Acidification Properties of a Fermented Milk Products Containing a Probiotic Strain of Lactobacillus Paracasei." International Dairy Journal, vol. 13, 2003, pp. 517-528.

Zhou, Xiaodan, et al., "Laxative Effect of Lactobacillus paracasei LC-01 on Constipation Mice." Science and Technology of Dairy Industry. 2012, vol. 35, No. 5, pp. 7-11.

* cited by examiner untreated

DNA from Bacteria $10^8$

Ferment

Sup from ferment

P31-43 liss

Sup from ferment 80C

GLUTEN-RELATED DISORDERS

CROSS-REFERENCE TO RELATED APPLICATIONS

This application claims the benefit of the filing date of U.S. Provisional Application No. 61/661,105, which was filed on Jun. 18, 2012, and U.S. Provisional Application No. 61/725,693, which was filed on Nov. 13, 2012, For the purpose of any U.S. application that may claim the benefit of U.S. Provisional Application No. 61/661,105 and U.S. Provisional Application No. 61/725,693, the contents of those earlier filed applications are hereby incorporated by reference in their entirety.

FIELD OF THE INVENTION

The present invention relates to probiotic organisms and compositions comprising metabolites produced by probiotic organisms. These compositions are useful or treatment of gluten-related disorders, for example, celiac disease.

BACKGROUND OF THE INVENTION

Gluten and gluten-related polypeptides are found in many cereal grains, including wheat, rye and barley. For individuals with gluten-related disorders such as celiac disease and gluten sensitivity, consumption of gluten-containing foods can have severe and long-lasting health consequences. Celiac disease is an autoimmune disorder of the small intestine that is triggered by gluten consumption in genetically predisposed people. Certain fragments of gluten ("gliadins") stimulate an immune response that permanently damages the small intestine and prevents nutrient absorption. Celiac disease can present with a wide spectrum of symptoms. The most common ones include chronic diarrhea, abdominal distention, weight loss, and failure to thrive (in children). Celiac disease can also be associated with iron deficiency anemia, osteoporosis, short stature, arthritis, infertility, peripheral neuropathy and liver failure. Celiac disease patients are also at increased risk for certain kinds of cancers, such as small bowel carcinomas and non-Hodgkin lymphoma. The incidence of celiac disease in populations of European descent is estimated to be between 0.5 and 1.5%. The incidence is increasing both in the U.S. and Europe, as well as in Asia, in part due to the adoption of westernized dietary patterns. Celiac disease is typically diagnosed in infancy or childhood, although the numbers of diagnoses made in adulthood is also on the rise. There is presently no cure for celiac disease and the standard treatment is a life-long restriction to a gluten-free diet.

Gluten sensitivity is less well-characterized than celiac disease. It presents with many of the same symptoms, but does not include the damage to the small intestine. The diagnosis tends to be made on exclusion criteria and improvement of symptoms once the patient is put on a gluten-free diet.

Adherence to a gluten-free diet requires strict avoidance of wheat, rye and barley products. This can be challenging given the often insufficient labeling information about the gluten content of foods; the opportunity for contamination during food processing and preparation, especially for those food prepared in outside the home; the financial burden of gluten-free products, and the willpower required for strict adherence. Compliance can also be affected by access to education and counseling, family and social support, and psychological factors. Moreover, strict adherence to a gluten-free diet can result in micronutrient deficiencies. Such deficiencies, particularly in the B vitamins (vitamin B6, vitamin B12 and folic acid) and certain trace elements, e.g., iron, zinc and copper, can result in potentially significant health issues, particularly in children. There is a continuing need for therapeutic agents for the treatment of gluten-related disorders.

SUMMARY OF THE INVENTION

The present invention provides compositions comprising one or more metabolites produced by *Lactobacillus paracasei* CBA L74, International Depository Accession Number LMG P-24778. The metabolites can reduce gliadin peptide toxicity in a subject having a gluten-related disorder. The metabolites, which are substantially stable to temperatures above standard physiological temperatures, reduce cellular entry of gliadin peptides. The gliadin peptide can vary and may include peptides that encompass one or more epitopes recognized by T-cells, e.g., P57-68, and peptides that are recognized by the innate immune system, e.g., P31-43. Exemplary peptides include α-gliadin peptides, for example, peptides having an amino acid sequence selected from the group consisting of LGQQQPFPPQQPY (SEQ ID NO: 1); QLQPFPQPQLPY (SEQ ID NO: 2); LGQQQPFP-PQQPYPQPQPF (SEQ ID NO: 3); and LQLQP-FPQPQLPYPQPQLPYPQPQLPYPQPQPF (SEQ ID NO: 4). In some embodiments, the metabolites are partially or substantially free of *Lactobacillus paracasei* CBA L74, International Depository Accession Number LMG P-24778, cells. The compositions can also include a physiologically acceptable carrier, for example, a food product or a pharmaceutical carrier.

Also provided are methods of treating a subject having a gluten-related disorder, the method comprising identifying a subject in need of treatment and administering an effective amount of a composition comprising a metabolite produced by *Lactobacillus paracasei* CBA L74, International Depository Accession Number LMG P-24778, wherein the metabolite reduces gliadin peptide toxicity. The methods and compositions are useful for the treatment of any gluten-related disorder, including celiac disease, including the various subtypes, e.g., classical celiac disease, atypical celiac disease, latent celiac disease, and silent celiac disease, dermatitis herptiformis, gluten ataxia and gluten sensitivity. The methods and compositions may be administered along with standard therapies for gluten related disorders, for example, dietary therapies.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 13a shows untreated control cells. FIG. 13b shows Caco2 cells treated with $10^4$ cfu/ml of *L. paracasei* CBA L74. FIG. 13c shows Caco2 cells treated with $10^6$ cfu/ml of *L. paracasei* CBA L74. FIG. 13d shows Caco2 cells treated with $10^8$ cfu/ml of *L. paracasei* CBA L74.

FIG. 15a shows untreated control cells. FIG. 15b shows Caco2 cells treated with $10^4$ cfu/ml of *L. paracasei* CBA L74. FIG. 15c shows Caco2 cells treated with $10^6$ cfu/ml of *L. paracasei* CBA L74. FIG. 15d shows Caco2 cells treated with $10^8$ cfu/ml of *L. paracasei* CBA L74.

FIG. 18a shows untreated control cells. FIG. 18b shows Caco2 cells treated with $10^8$ cfu/ml of *L. paracasei* CBA L74. FIG. 18c shows Caco2 cells treated with supernatant collected from $10^8$ cfu/ml of *L. paracasei* CBA L74.

FIG. 20a shows untreated control cells. FIG. 20b shows Caco2 cells treated with $10^8$ cfu/ml of *L. paracasei* CBA L74. FIG. 20c shows Caco2 cells treated with supernatant collected from $10^8$ cfu/ml of *L. paracasei* CBA L74.

FIG. 20a shows untreated control cells. FIG. 20b shows Caco2 cells treated with supernatant collected from the equivalent of $10^8$ cfu/ml of *L. paracasei* CBA L74.

FIG. 20a shows untreated control cells. FIG. 20b shows Caco2 cells treated with *L. paracasei* CBA L74 supernatant. FIG. 20c shows Caco2 cells treated *L. paracasei* CBA L74 supernatant that had been removed.

FIG. 26a shows untreated control cells. FIG. 26b shows Caco2 cells treated with *L. paracasei* CBA L74 supernatant. FIG. 26c shows Caco2 cells treated *L. paracasei* CBA L74 supernatant that had been boiled. FIG. 26d shows Caco2 cells treated *L. paracasei* CBA L74 supernatant that had been heated at 80° C.

DETAILED DESCRIPTION OF THE PREFERRED EMBODIMENT

Figure 1:
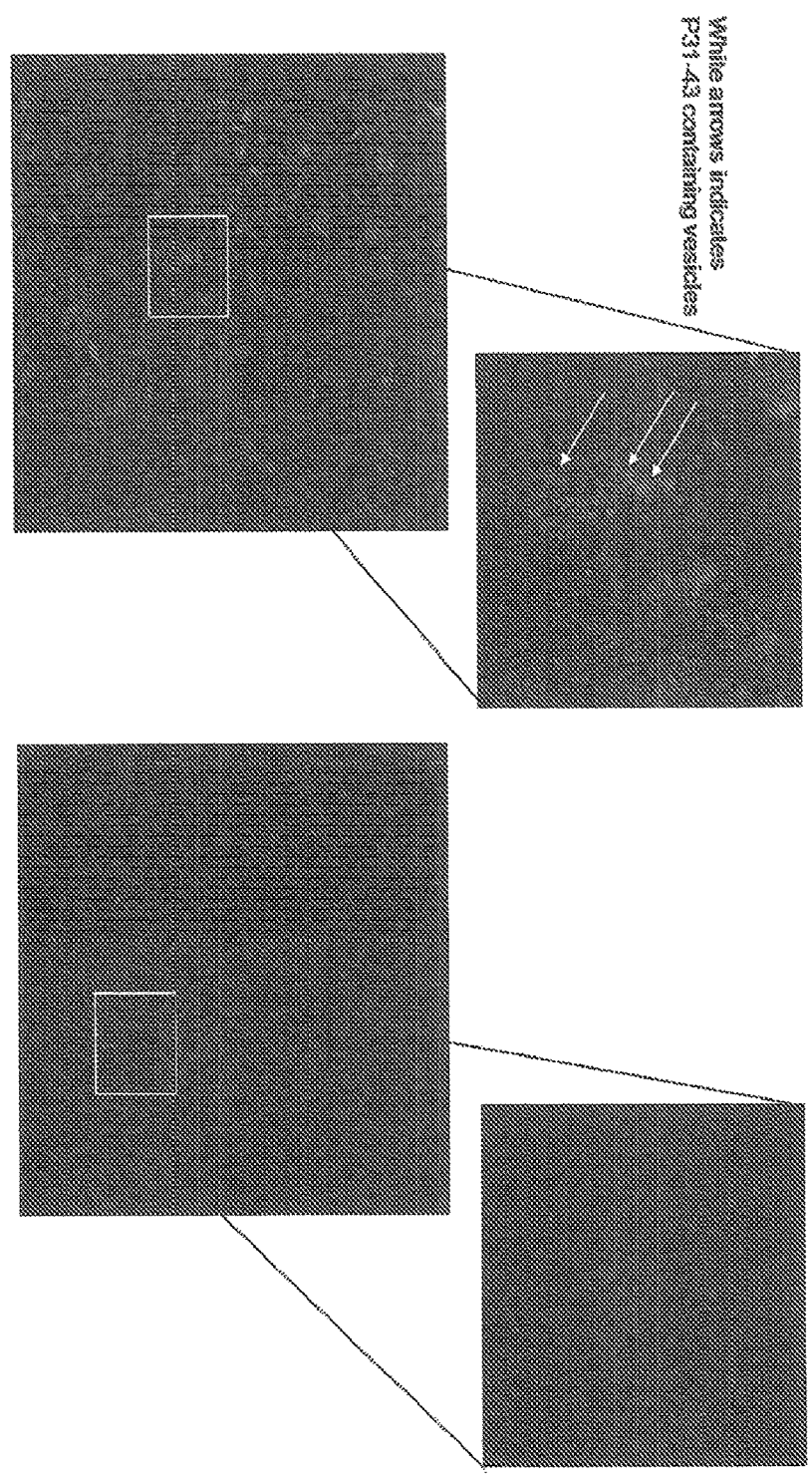
FIG. 1 is an analysis of the effect of *Lactobacillus paracasei*, strain CBA L74 on entry of P31-43$^{liss}$ into CaCo2 cells.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. When only a single machine is illustrated, the term "machine" shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures.

The present invention is based, in part, on the inventors' discovery that cultures of the probiotic organism *Lactobacillus paracasei*, strain CBA L74, can reduce the entry of certain components of gluten into human intestinal cells. More specifically, the inventors have found that isolated *L. paracasei* CBA L74 and culture supernatants from *L. paracasei* CBA L74 reduced the entry of α-gliadin peptides into cultured human intestinal epithelial cells. Moreover, the reduction in peptide entry was also observed for foods that had been fermented by *L. paracasei* CBA L74. The effect on peptide entry was observed even when culture supernatants were treated with heat. Accordingly, the invention features compositions that can mitigate the toxic effects of gliadin peptides. The compositions can include *Lactobacillus paracasei*, strain CBA L74 cells, metabolites produced by *Lactobacillus paracasei*, strain CBA L74, or a combination of *Lactobacillus paracasei*, strain CBA L74 cells and metabolites produced by *Lactobacillus paracasei*, strain CBA L74.

*Lactobacillus paracasei*, strain CBA L74 was isolated by the inventors and deposited under the Budapest Treaty on the International Recognition of the Deposit of Microorganisms for the Purposes of Patent Procedure on Sep. 9, 2008 at the Belgian Coordinated Collections of Microorganisms (BCCM) Laboratorium voor Microbiologie (LMG), Ghent, Belgium. The Accession Number given by the International Depositary Authority is LMG P-24778. For ease of reading, we will not repeat the phrase "Accession Number LMG P-24778" on every occasion. It is to be understood that where we refer to *L. paracasei*, strain CBA L74, we refer to the deposited strain having the Accession Number LMG P-24778.

While we believe we understand certain events that occur upon administration of compositions comprising or made by fermentation with *L. paracasei* CBA L74, the compositions of the present invention are not limited to those that work by affecting any particular cellular mechanism. Our working hypothesis is that compositions comprising *L. paracasei* CBA L74, supernatant from *L. paracasei* CBA L74 cultures or fermentates, and metabolites produced by *L. paracasei* CBA L74 may provide an increased barrier to translocation of gluten and gluten-related polypeptides across the intestinal mucosa and thus moderate the effects of gluten and gluten-related peptides in individuals having a gluten related disorder, for example, celiac disease or gluten sensitivity. The inventors have found that *L. paracasei* CBA L74, supernatant reduced cellular uptake of molecules that enter cells via different endocytotic pathways, e.g., phagocytosis, macropinocytosis, clathrin-mediated endocytosis (also referred to as receptor-mediated endocytosis) and caveolae. For example, *L. paracasei* CBA L74, supernatant reduced cellular entry of both dextran, which is known to enter cells via macropinocytosis, and epidermal growth factor (EGF), which enters cells via receptor-mediated endocytosis. The beneficial effects of the compositions described herein may derive for example, from metabolites produced during fermentation, for example, organic acids such as lactic acid, butyric acid or acetic acid. Alternatively or in addition, bacterial cell wall fragments and other sub-cellular bacterial components, such as proteins, carbohydrates, nucleic acid fragments and lipids, may exert effects on the cellular response to gluten and gluten-related polypeptides.

Accordingly, the invention features compositions and methods that can be used to protect cells from the potentially toxic effects of gluten and gluten-related peptides. The compositions can include media in which *L. paracasei* CBA L74 have been grown or food products, e.g., dairy products or cereal products, that have been fermented by *L. paracasei* CBA L74. In some embodiments, the media or food products can be treated, e.g., by physico-chemical methods such as centrifugation, to remove all or substantially all of the *L. paracasei* CBA L74 cells that had been cultured in the media or food product. In some embodiments, the compositions can include isolated *L. paracasei* CBA L74 and a physiological carrier. The carrier may be a food product, but the invention is not so limiting and in some embodiments the carrier may be a pharmacological carrier.

Also provided are methods of making and using the compositions. The methods of the invention include methods of producing compositions comprising *L. paracasei* CBA L74, methods of fermenting food products with *L. paracasei* CBA L74 and methods of administering the compositions to a subject having a gluten-related disorder. The methods can be used on human subjects or in veterinary medicine. Regardless of the subject (whether human or non-human), any of the present methods can include a step of identifying the subject. For example, the methods can include a step of determining whether the subject is in need of treatment.

Compositions

*L. Paracasei* CBA L74

The compositions of the invention can include the probiotic organism, *L. paracasei* CBA L74. The World Health Organization has defined probiotics as: "Live microorganisms which when administered in adequate amounts confer a health benefit on the host." In some embodiments, the *L. paracasei* CBA L74 can be subjected to treatments that render them non-replicating, for example, exposure to heat, γ-irradiation, or uv-irradiation. A non-replicating *L. paracasei* CBA L74 can be a dead cell or a living cell that has been rendered incapable of cell division. A non-replicating *L. paracasei* CBA L74 can be an intact cell or a cell that has undergone partial or complete lysis. In some embodiments, the non-replicating cells can include a mixture of intact and lysed cells.

In some embodiments, the compositions can include *L. paracasei* CBA L74 fermetates, from which all or substantially all, of the *L. paracasei* CBA L74 cells have been removed. Methods for separating cells from growth media are well known in the art and can rely upon physical methods, for example, centrifugation to produce a cell pellet and a culture supernatant, filtration, ultrafiltration, tangential flow-filtration, normal flow filtration or reverse osmosis. Alternatively or in addition, the separation method can be ligand-based and include, for example, an antibody that specifically binds to L. paracasei CBA L74. The antibody can be coupled to a solid support such as a magnetic bead.

The compositions include one or more L. paracasei CBA L74 metabolites, i.e., any substance produced by L. paracasei CBA L74 The metabolite may be encoded by one or more genes or it may be generated by the enzymatic activity of one or more gene products. Metabolites include, for example, small molecules, e.g., amino acids, nucleosides, nucleotides as well as larger polymeric structures such as polypeptides, carbohydrates, nucleic acids, proteoglycans and lipids. The metabolite can be a primary metabolite, e.g., a metabolite directly involved in normal cell function, or a secondary metabolite, e.g., a metabolite typically not required for fundamental cellular functions. A metabolite can also include any metabolic intermediate generated during the synthesis of a primary or secondary metabolite. Intermediates can include, but are not limited to intermediates of the Embden-Meyerhof pathway, the pentose phosphate (pentose-P) pathway, the Entner-Doudoroff pathway, the citrate cycle, and amino acid biosynthesis.

Exemplary primary metabolites include, without limitation, alcohols, e.g., ethanol, methanol, butanol; amino acids, e.g., lysine, arginine, ornithine, histidine, citrulline, isoleucine, alanine, valine, leucine, glycine, threonine, serine, proline, phenylalanine, tyrosine, tryptophan, cysteine, cystine, methionine, glutamic acid, aspartic acid, glutamine, and asparagine; nucleotides, e.g., 5' guanylic acid; antioxidants, e.g., isoasorbic acid; organic acids, e.g., acetic acid, lactic acid, citric acid, formic acid; vitamins, e.g., vitamin B12; sugars, fatty acids, e.g., short chain fatty acids; polyamines; peptides, e.g., bacteriocins such as a lantibiotic e.g. nisin, or a nonlantibiotic, e.g., enterocin, plantaricin W, plantaricin S.

A metabolite can also be a secondary metabolite. Secondary metabolites are typically those that are not required for fundamental cellular functions. Secondary metabolites can vary widely; exemplary secondary metabolites include antibiotics, hormones, flavonoids, terpenoids, alkaloids, phenylpropanoids, phenyl derivatives, hexanol derivatives, coumarins, stilbenes, cyanohydrins, glucosinolates, sterols, and saponins.

Lactobacilli typically produce the following metabolites during the fermentation of milk products: lactic acid/lactate, acetate, ethanol, formate, acetaldehyde, α-acetolactate, acetoin, diacetyl, and 2,3 butylene glycol (butanediol) during the fermentation of milk products. Fermentation can be any process in which a microbe causes or contributes to a breakdown of a complex organic substance into simpler substances.

The L. paracasei CBA L74 metabolite can be contained within media, fermentates or culture supernatants. In some embodiments, the metabolite can be partially or substantially isolated from the media, fermentates or culture supernatants. Thus, the functional metabolite, i.e., a metabolite that reduces cell entry of a gliadin peptide, can include or exclude any of the metabolites described above. Methods of isolation of metabolites will vary according to the structure and chemistry of the particular metabolite. A partially or substantially isolated metabolite will retain the functional activity, i.e., the ability to reduce cell entry of gliadin peptides, of media, fermentates or culture supernatants. Thus, if an L. paracasei CBA L74 culture supernatant can reduce gliadin peptide entry into cells, it is expected that a partially or substantially isolated metabolite from L. paracasei CBA L74 culture supernatant will also reduce gliadin peptide entry into cells. Standard art-known methods can be used for isolation and characterization of L. paracasei CBA L74 metabolites. Exemplary methods include, for example, stability analyses, e.g., stability to heat, pH, and/or enzymatic activity; chromatographic analysis, e.g., size exclusion chromatography, high performance liquid chromatography (HPLC), gas chromatography, thin layer chromatography, ion exchange chromatography, affinity chromatography, reverse phase chromatography; mass spectrometry. In some embodiments, the metabolite is stable to heat, that is, it retains its functional activity, i.e., the ability to prevent cell entry of gliadin peptides, after exposure to temperatures outside the normal physiological range, e.g., 50° C., 60° C., 70° C., 80° C., 90° C. or 100° C.

Gluten and Gluten-Related Polypeptides

Regardless of the particular form, the compositions described herein reduce cellular uptake of gluten and gluten-related polypeptides. Gluten and gluten-related polypeptides are the major storage proteins of dietary cereal grains. Gluten is found in wheat. The closely related proteins, the hordeins and the secalins are found in barley and rye, respectively. Several hundred genes encoding gluten and gluten-related proteins have been described. In addition to its nutritional properties, gluten plays a key role in determining the unique baking quality of wheat by conferring water absorption capacity, cohesivity, viscosity and elasticity on dough. Gluten actually is a complex of two polypeptide fractions that have been classified based on their solubility in aqueous alcohols: the soluble gliadins and the insoluble glutenins. Both fractions consist of numerous, related protein components characterized by a high glutamine and proline content.

Gliadins are monomeric proteins with molecular weights (MWs) around 28,000-55,000 and isoelectric points of about pH 3.0-4.0. There are four classes of gliadin polypeptides: α-gliadin, β-gliadin, γ-gliadin and ω-gliadin. Exemplary amino acid sequences for α-gliadin can be found in GenBank at GI:7209265 (Triticum aestivum 290 amino acids, SEQ ID NO: 7); GI:7209263 (Triticum aestivum 269 amino acids, SEQ ID NO: 8); GI:376341626 (Triticum aestivum 210 amino acids, SEQ ID NO: 9); GI:282721198 Triticum durum, 313 amino acids, SEQ ID NO: 10).

Glutenin is a larger, multimeric protein ranging in MW from about 100,00 to more than 10,000,000 with an average MW of about 3,000,000. Isoelectric points for glutenin range from about 6.5-7.0. After reduction of disulphide bonds, the resulting glutenin subunits show a solubility in aqueous alcohols similar to gliadins. Based on primary structure, glutenin subunits have been divided into the high-molecular-weight (HMW) subunits (MW=67,000-88,000) and low-molecular-weight (LMW) subunits (MW=32,000-35,000). Gliadins, glutenins, hordeins, and secalins have a high proline and glutamine content. The high proline content renders these proteins resistant to complete proteolytic digestion by gastric, pancreatic, and brush border enzymes in the human intestine, since those enzymes are deficient in prolyl endopeptidase activity. This can result in the accumulation of relatively large peptide fragments (as many as 50 amino acids in length) with a high proline and glutamine content in the small intestine.

The specific amino acid sequences for gliadin can vary, but they all contain T-cell epitopes that trigger the immune responses involved in celiac disease pathogenesis. It is these gluten specific T cell responses in the small intestine play an important role in producing the inflammatory response that ultimately results in the hallmark atrophy of intestinal villi and crypt hyperplasia. Specific native gluten peptides can bind to HLA-DQ2/8, the HLA types most strongly associated with celiac disease. This HLA binding induces lamina propria CD4 T cell responses, which in turn damage the mucosa of the small intestine. Tissue damage initiates secretion of the wound-healing enzyme tissue transglutaminase (tTG). However, tTG also deamidates gluten peptides. Deamidation converts neutral glutamine residues to negatively charged glutamic acid residues. These deamidated peptides have significantly increased binding affinity for HLA-DQ2/8 relative to peptides that have not been deamidated. This process leads to an enhanced antigenic presentation of gliadin. Binding of deamidated peptides further activates gluten-specific CD4+ T-helper 1 (Th1) cells in the lamina propria, which in turn increases intraepithelial lymphocytosis, crypt hyperplasia, production of cytokines leading to villous atrophy, and expansion of B cells that produce antibodies to gliadin and tTG.

Multiple T cell epitope motifs have been identified in α- and γ-gliadins as well as in glutenins. The majority of these showed enhanced T cell recognition after deamidation. Moreover, celiac disease patients are generally sensitive to more than one gluten peptide. Although the DQ2/8 interaction represents the most significant association with celiac disease so far defined, non-immunogenic gluten peptides can also have an impact on the innate immune system.

Gliadin peptides P31-43 and P31-49 are generally not recognized by T cells. These peptides induce an innate immune response in the celiac mucosa. Peptide P31-43 delays endocytic vesicle maturation and consequently reduces epidermal growth factor receptor (EGFR) degradation and prolongs EGFR activation. The prolonged EGFR activation has been shown to induce increased cell proliferation and actin modifications in both celiac crypt enterocytes and in cultured cell lines. Upon entry into intestinal enterocytes or the human intestinal cell line, CaCo2, P31-43 interacts with early endocytic vesicles, reduces their motility and delays their maturation to late endosomes.

Different gluten peptides are involved in the celiac disease process. There are two groups of biologically-active peptides that derive from α-gliadin. The serine-containing group of peptides appears to be essentially cytotoxic, while the tyrosine-containing group has the capacity to trigger immunological reactions in celiac disease patients. The activity of the serine-containing peptides is linked to the presence of PSQQ and QQQP motifs. The tyrosine-containing peptides, e.g., QQPY and/or QPYP are associated with immunological activity.

Gliadin peptides can vary widely in sequence. A polypeptide that has a sequence that is identical to a portion of a gliadin sequence and that functions (e.g., for one or more of the purposes described herein) is a gliadin peptide. A full length gliadin includes a gliadin peptide sequence and one or more of the peptides described herein may lie partially or wholly within the gliadin sequence. A peptide that has a sequence that differs to a certain limited extent from a sequence that is found in a naturally occurring gliadin and that retains the ability to function (e.g., retains sufficient activity to confer gliadin peptide toxicity) is a biologically active variant of a gliadin peptide. We tend to use the terms "gliadin" to refer to full-length, naturally-occurring gliadin proteins, and we tend to use the terms "polypeptide" and "peptide" when referring to fragments thereof (i.e., to fragments of gliadin) and biologically active variants thereof. Because the polypeptides or peptides can have a sequence that is identical to a sequence found in gliadin, the polypeptides or peptides are derived from fragments of gliadin.

While the sequences of the present polypeptides can vary, useful polypeptides can include fragments of SEQ ID NOs: 7-10. The polypeptides can include or consist of an amino acid sequence of a gliadin that is naturally expressed in a plant cell. A biologically active variant can include, for example, an amino acid sequence that differs from a wild-type fragment of a gliadin by virtue of containing one or more conservative amino acid substitutions. In some embodiments, at least 50% of the amino acid residues of the variant are identical to residues in the corresponding wild-type fragment of a gliadin. Biologically active variants can also include amino acid sequences that differ from a wild-type fragment of a gliadin by virtue of non-conservative amino acid substitutions, additions, and/or deletions.

We refer to certain amino acid sequences as "polypeptides" to convey that they are linear polymers of amino acid residues, and to help distinguish them from full-length proteins. It will be understood that the polypeptides can therefore include only a fragment of a gliadin (or a biologically active variant thereof) but may include additional residues as well. The polypeptides of the invention can vary in length. For example, the polypeptides can be 8-40 (e.g., 12, 14, 16, 18, or 20) amino acids long or longer (e.g., up to about 40 residues).

The polypeptides that are biologically active variants of a gliadin can be characterized in terms of the extent to which their sequence is similar to or identical to the corresponding fragment of the gliadin. For example, the sequence of a biologically active variant can be at least or about 60% identical to corresponding residues in a wild type gliadin. For example, a biologically active variant of a gliadin polypeptide can have an amino acid sequence with at least or about 60% sequence identity (e.g., at least or about 65%, 70%, 75%, 80%, 85%, 90%, 95%, 97%, 98%, or 99% sequence identity) to a gliadin (e.g., to the amino acid sequence set forth in SEQ ID NO: 7-10 or to another polypeptide as described herein (e.g., a polypeptide represented by, for example, SEQ ID NOs:1-6) or to a homolog or ortholog thereof).

A biologically active variant of a gliadin polypeptide will retain sufficient biological activity to confer toxicity in a subject having a gluten-related disorder. The biological activity can be assessed in ways known to one of ordinary skill in the art and includes, without limitation, cellular uptake assays, gene expression assays, or in vivo animal models. Biologically active variants can be identified, for example, by comparing the relative activities of the variant polypeptide with that of an active fragment of a gliadin peptide. The assays can include an unrelated control polypeptide (e.g., one could include in any given assay a peptide that has the same amino acid content randomly arranged, as well as a vehicle-only control). Some biologically active variants may even have greater biological activity than the cognate, naturally occurring fragment or a full-length gliadin. More specifically, a biologically active variant can have at least or about 30%, 40%, 50%, 60%, 70%, 80%, 90%, 95%, 98%, or more of the biological activity of the native form polypeptide.

Exemplary α-gliadin peptides that play a role in celiac disease include P31-43, LGQQQPFPPQQPY, (SEQ ID NO.: 1); P31-49 LGQQQPFPPQQPYPQPQPF (SEQ ID NO: 3); P44-55; PQQPFPSQLP (SEQ ID NO.: 5; P57-68 QLQP-FPQPQLPY (SEQ ID NO.: 2); P56-88, LQLQP-FPQPQLPYPQPQLPYPQPQLPYPQPQPF (SEQ ID NO: 4) and P63-76 QPQLPYPQPQLPYP (SEQ ID NO.: 6).

Food Products

The compositions of the invention can include a physiologically acceptable carrier. The physiologically acceptable carrier can be a food product or a pharmaceutical carrier. We use the terms "physiologically acceptable" (or "pharmacologically acceptable") to refer to molecular entities and compositions that do not produce an adverse, allergic or other untoward reaction when administered to an animal or a human, as appropriate. Thus, the compositions of the invention include food products fermented by the probiotic organism, *L. paracasei* CBA L74. The food product may include *L. paracasei* CBA L74 cells, either live or non-replicating. In some embodiments the food product can be processed to remove all or substantially all the *L. paracasei* CBA L74 cells. Any food product amenable to fermentation by *L. paracasei* CBA L74 may be used. The food product can be a dairy product, for example, milk or a milk-based product. Exemplary milk sources include, without limitation, cattle, sheep, goats, yaks, water buffalo, horses, donkeys, reindeer and camels. Regardless of the source, the milk or milk products can be in any form suitable for fermentation by *L. paracasei* CBA L74. For example, the milk can be whole milk or milk that has been processed to remove some or all of the butterfat, e.g., 2% milk, 1% milk or no-fat milk. Alternatively or in addition, the milk can be previously pasteurized and or homogenized, dried and reconstituted, condensed or evaporated. Fractions of milk products including casein, whey protein or lactose may also be used. In some embodiments, the milk product can be from about 1% to about 30% reconstituted skim milk powder, for example about 2%, about 5%, about 7%, about 9%, about 10%, about 12%, about 15%, about 20%, about 25%, about 30% reconstituted skim milk powder. Prior to fermentation the milk product can be combined with one or more of the following: a) a carbohydrate (e.g., a disaccharide such as dextrose or a starch; b) a lipid; c) a vitamin and d) a mineral. For example, skim milk powder may be combined with dextrose to about 2%, e.g., about 0.25%, about 0.50%, about 0.75%, about 1.0%, about 1.5% or about 2.0%.

The food product can be a cereal product, for example, rice, oats, corn, sorghum, or millet. In some embodiments, the cereal product may be wheat, barley, rye or triticale. The cereal product can be a whole grain or be milled into a flour. The food product can be a single kind of cereal or a mixture of two or more kinds of cereals, e.g., oat flour plus rice flour. The cereal products can be of a grade and type suitable for human consumption or can be products suitable for consumption by domestic animals. Generally, the cereal product is hydrated prior to fermentation. The concentration of cereal can vary, but useful ranges include from about 5% to about 50% weight/volume, for example, about 8% weight/volume, about 10% weight/volume, about 12% weight/volume, about 15% weight/volume, about 18% weight/volume, about 20% weight/volume, about 22% weight/volume, about 25% weight/volume, about 30% weight/volume, about 35% weight/volume, about 40% weight/volume, about 45% weight/volume or about 50% weight/volume. Exemplary concentrations include 15% weight/volume of rice or a mixture of 18.5% weight/volume oat flour plus 5% weight/volume of malted barley flour. The pH of the hydrated cereals may be adjusted using any acid suitable for consumption. The acid can be, for example, an organic acid. Useful organic acids include acetic acid, citric acid, lactic acid, adipic acid, malic acid and tartaric acid. Any combination of two or more acids can be used. In some embodiments, the pH may be adjusted to about 4.0 using citric acid.

The food product can also be a vegetable or a fruit product, for example, a juice, a puree, a concentrate, a paste, a sauce, a pickle or a ketchup. Exemplary vegetables and fruits include, without limitation, squashes, e.g., zucchini, yellow squash, winter squash, pumpkin; potatoes, asparagus, broccoli, Brussels sprouts, beans, e.g., green beans, wax beans, lima beans, fava beans, soy beans, cabbage, carrots, cauliflower, cucumbers, kohlrabi, leeks, scallions, onions, sugar peas, English peas, peppers, turnips, rutabagas, tomatoes, apples, pears, peaches, plums, strawberries, raspberries, blackberries, blueberries, lingonberries, boysenberries, gooseberries, grapes, currants, oranges, lemons, grapefruit, bananas, mangos, kiwi fruit, and carambola.

The food product can also be a "milk" made from tree nuts or legumes, for example, soymilk or almond milk.

Also contemplated are food products comprising animal proteins, for example, meat, for example, sausages, dried meats, fish and dried fish products.

Regardless of the type of food product that is used, the product is combined with *L. paracasei* CBA L74 and incubated at a temperature and for a time sufficient for fermentation to occur. Any standard fermentation method known in the art may be used. Specific fermentation conditions will vary according to many factors including, for example, the type of food product, the concentration of the food product, the instrumentation that is used, the sample volume, the initial concentration of the *L. paracasei* CBA L74 inoculum, the presence, if any, of a co-inoculum, the organoleptic properties of the fermented food, and the intended use of the fermented food.

Both the instrumentation and the substrate (i.e., the food product to be fermented) are sterilized prior to inoculation with *L. paracasei* CBA L74 in order to decrease the level of, or eliminate, viable bacteria and/or fungi and/or infectious viruses. The instrumentation can be sterilized using standard methods or according to the manufacturer's instructions. Choice of a particular method for sterilization of the substrate will depend, in part, on the stability of the substrate to the sterilization method. For example, the substrate can be sterilized by steam and pressure, e.g. by autoclaving, repeated cycles of heating and cooling (e.g., tyndalization) exposure to high pressures (e.g., pascalization), ultrafiltration, or radiation (e.g., exposure to gamma-, x-, e-beam, and/or ultra-violet (wavelength of 10 nm to 320 nm, e.g., 50 nm to 320 nm, 100 nm to 320 nm, 150 nm to 320 nm, 180 nm to 320 nm, or 200 nm to 300 nm). Aliquots of the substrate can be removed following treatment and plated on suitable media to confirm the absence of bacterial and/or fungal contaminants. If the substrate has been sterilized by exposure to high temperatures, it should be cooled to at least 37° C. prior to inoculation with *L. paracasei* CBA L74.

The substrate can be inoculated with *L. paracasei* CBA L74 according to standard methods, for example, from fresh liquid culture or a freeze-dried culture that has been resuspended in aqueous medium for a short time prior to inoculation. In general, *L. paracasei* CBA L74 are added at concentrations of about $0.5 \times 10^6$ to about $1 \times 10^6$ cfu/ml of substrate, e.g., about $1 \times 10^6$ cfu/ml, about $2 \times 10^6$ cfu/ml, about $5 \times 10^6$ cfu/ml, $7 \times 10^6$ cfu/ml $8 \times 10^6$ cfu/ml. The culture should be agitated sufficiently to produce a relatively uniform distribution of bacteria and substrate, but not excessively since *L. paracasei* CBA L74 is an anaerobic bacterium. For example, a five liter culture may be agitated at about 150 rpm. Fermentation temperature is generally at 37° C. Various parameters, for example, the pH, the partial pressure of $O_2$, stirrer speed, temperature, gas mixing, foam level and substrate concentration can be monitored during fermentation and adjusted accordingly. Growth of the *L. paracasei* CBA L74 can be monitored using standard microbiological methods. Fermentation is carried out until the concentration of *L. paracasei* CBA L74 is about between about $10^8$/ml and about $10^9$/ml. Depending upon the substrate and other conditions, this concentration may be reached in about 10 to about 30 hours after inoculation, e.g., about 12 hours, about 15 hours, about 18 hours, about 24 hours, about 30 hours.

Samples of the substrate can be assayed before, during and after fermentation for quality assurance using standard microbiological methods. Exemplary methods include, but are not limited to, growth on Rogosa agar for *L. paracasei* CBA L74, growth on plate count agar (PCA) for total aerobes, growth on McConkay agar for coliforms, growth on reinforced clostridial agar (RCM) for Clostridia. In addition to colony counts, colony morphologies can be observed and compared to reference samples.

In some embodiments, a co-inoculum can be added along with the *L. paracasei* CBA L74 in order to help initiate fermentation. Useful co-inocula for fermentation of milk products include, for example, without limitation, *Streptococcus thermophilus, Lactobacillus paracasei, Lactobacillus salivarious, Lactobacillus rhamnosus, Lactobacillus casei, Lactobacillus lactis, Lactobacillus delbrueckii*, subsp. *Bulgaricus, Lactobacillus acidophilus, Lactobacillus brevis*, or *Leuconostoc mesenteroides*. In general, the concentration of the co-inoculum will be lower than that of *L. paracasei* CBA L74, for example, about $1\times10^4$/ml$\times10^5$/ml. The final concentration of *S. thermophilus* can range from about $0.5\times10^8$/ml to about $2.5\times10^8$/ml.

Once suitable concentrations of *L. paracasei* CBA L74 have been reached, the fermented food can be further processed for use. In some embodiments, the fermented food can be fractionated to remove all or substantially all of the *L. paracasei* CBA L74 cells. In some embodiments, the pH of the fermented food can be adjusted, for example from about 3.0 to nearer to neutrality, e.g., 6.5, with the addition of NaOH or KOH. In some embodiments the fermented food can be dried. The fermented food product can be dried by any method known in the art that will result in the retention of immunomodulatory properties of the fermented food. Exemplary drying methods include spray drying, freeze-drying e.g., lyophilization, or drum-drying. The final water content of the fermented food product may vary but can be between about 1% and about 10% or more. In some embodiments, the drying process can render the *L. paracasei* CBA L74 non-replicating.

The dried fermented foods can be hydrated before use. Depending on the amount of liquid used in the hydration, the fermented food products may contain the equivalent of about $10^2$, about $10^3$, about $10^4$, about $10^5$, about $10^6$, about $10^7$, about $10^8$, about $10^9$, about $10^{10}$, about $10^{11}$ and, about $10^{12}$ cfu/ml of *L. paracasei* CBA L74. The dried *L. paracasei* CBA L74 do not form colonies, so it is understood that this amount is calculated based on the number of live bacteria that were present in the fermented foods prior to the drying step. In some embodiments, the fermented food products may include the equivalent of about $10^7$ to about $10^{12}$ cfu/g, e.g., about $5\times10^7$ cfu/g, about $1\times10^8$ cfu/g, about $5\times10^8$ cfu/g, about $1\times10^9$ cfu/g, about $5\times10^9$ cfu/g, about $1\times10^{10}$ cfu/g, about $5\times10^{10}$ cfu/g, about $1\times10^{11}$ cfu/g, about $5\times10^{11}$ cfu/g of dry weight.

Two or more fermented food products prepared by the methods of the invention may be combined prior to administration. For example, fermented milk products may be combined with fermented cereal products. Alternatively, the fermented food product can be combined with other food products, for example, non-fermented food products or food products fermented using other bacterial strains. Any combination can be used provided that the effects on gliadin peptides of the fermented food are retained. Exemplary food products include, without limitation, dairy products, e.g., milk, yoghurt, curd, cheese and cheese-based products, fermented milks, milk-based fermented products, milk-based powders, infant formulae, milk-based strained infant foods, ice cream, gelato, puddings, soups, sauces, purees, or dressings, nutritional formulas for the elderly; cereal products e.g., pablum, cereal-based strained infant foods, oatmeal, farina, semolina, polenta, pasta, biscuits, crackers, energy bars; vegetable products, e.g., purees, vegetable-based strained infant foods, pickled vegetables including cucumbers, cabbage, carrots, beans, peppers, or relishes; fruit products, e.g., fruit-based strained infant foods, tomato products, purees, sauces, pastes, ketchups, fruit purees; or a protein-based products, e.g., legumes, sausages, lunch meats, hot dogs, or pureed meats. In some embodiments the fermented food may be combined with pet foods or animal feeds.

Pharmaceutical Compositions

The compositions described herein may be combined with a pharmaceutically acceptable carrier. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

Thus, the invention also includes pharmaceutical compositions which contain, as the active ingredient, the *L. paracasei* CBA L74 or one or more metabolites produced by *L. paracasei* CBA L74 described herein, in combination with one or more pharmaceutically acceptable carriers. In some embodiments, the *L. paracasei* CBA L74 can be sterilized using conventional sterilization techniques before or after it is combined with the pharmaceutically acceptable carrier. In making the compositions of the invention, the *L. paracasei* CBA L74 or one or more metabolites produced by *L. paracasei* CBA L74, are typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. As is known in the art, the type of diluent can vary depending upon the intended route of administration. The resulting compositions can include additional agents, such as preservatives. The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary). Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

Pharmaceutically acceptable compositions for use in the present methods, including those in which *L. paracasei* CBA L74 or one or more metabolites produced by *L. paracasei* CBA L74, are entrapped in a colloid for oral delivery, can be prepared according to standard techniques. The *L. paracasei* CBA L74 or one or more metabolites produced by *L. paracasei* CBA L74, can be dried and compacted by grinding or pulverizing and inserted into a capsule for oral administration. In some embodiments, the *L. paracasei* CBA L74 or one or more metabolites produced by *L. paracasei* CBA L74, can be combined one or more excipients, for example, a disintegrant, a filler, a glidant, or a preservative. Suitable capsules include both hard shell capsules or soft-shelled capsules. Any lipid-based or polymer-based colloid may be used to form the capsule. Exemplary polymers useful for colloid preparations include gelatin, plant polysaccharides or their derivatives such as carrageenans and modified forms of starch and cellulose, e.g., hypromellose. Optionally, other ingredients may be added to the gelling agent solution, for example plasticizers such as glycerin and/or sorbitol to decrease the capsule's hardness, coloring agents, preservatives, disintegrants, lubricants and surface treatment. In some embodiments, the capsule does not include gelatin. In other embodiments, the capsule does not include plant polysaccharides or their derivatives.

Regardless of their original source or the manner in which they are obtained, the *L. paracasei* CBA L74 or one or more metabolites produced by *L. paracasei* CBA L74, can be formulated in accordance with their use. These compositions can be prepared in a manner well known in the pharmaceutical art, and can be administered by a variety of routes, depending upon whether local or systemic treatment is desired and upon the area to be treated. Administration may be oral or topical (including ophthalmic and to mucous membranes including intranasal, vaginal and rectal delivery). In some embodiments, administration can be pulmonary (e.g., by inhalation or insufflation of powders or aerosols, including by nebulizer; intratracheal, intranasal, epidermal and transdermal) or ocular. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

The compositions can be formulated in a unit dosage form, each dosage containing, for example, from about 0.005 mg to about 2000 mg of *L. paracasei* CBA L74 or one or more metabolites produced by *L. paracasei* CBA L74, per daily dose. In some embodiments, the compositions may contain the equivalent of about $10^2$, about $10^3$, about $10^4$, about $10^5$, about $10^6$, about $10^7$, about $10^8$, about $10^9$, about $10^{10}$, about $10^{11}$ and, about $10^{12}$ cfu/ml of *L. paracasei* CBA L74. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.005 mg to about 1000 mg of the *L. paracasei* CBA L74 or one or more metabolites produced by *L. paracasei* CBA L74, of the present invention.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient.

In some embodiments, tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The proportion or concentration of the compositions of the invention in a pharmaceutical composition can vary depending upon a number of factors including dosage, chemical characteristics (e.g., hydrophobicity), and the route of administration. For example, the *L. paracasei* CBA L74 or one or more metabolites produced by *L. paracasei* CBA L74, of the invention can be provided in a capsule containing from about 0.005 mg gram to about 1000 mg for oral administration.

Methods of Use

Gluten-Related Disorders

The compositions disclosed herein are generally and variously useful for treatment of gluten-related disorders. Subjects for whom such treatment is beneficial include those who experience or who are at risk for toxic effects upon ingestion of gluten and gluten-related polypeptides. Such toxic effects can encompass a wide spectrum of symptoms including, but not limited to inflammation, autoimmune reactions, gastrointestinal symptoms such as diarrhea, steatorrhea, abdominal distension, weight loss, anemia, osteoporosis, arthritis, infertility, peripheral neuropathy, liver failure, and depression. Gliadin peptide toxicity can stem from cytotoxic or immunological mechanisms or a combination of cytotoxic and immunological mechanisms. A symptom of gliadin peptide toxicity can include inflammation, autoimmune reactions, gastrointestinal symptoms such as diarrhea, steatorrhea, abdominal distension, weight loss, anemia, osteoporosis, arthritis, infertility, peripheral neuropathy, liver failure, and depression. Gluten-related disorders include celiac disease, including the various subtypes, e.g., classical celiac disease, atypical celiac disease, latent celiac disease, and silent celiac disease, dermatitis herptiformis, gluten ataxia and gluten sensitivity.

The subtypes of celiac disease include classical celiac disease, atypical celiac disease, latent celiac disease, and silent celiac disease. The classical symptoms associated with celiac disease are diarrhea, abdominal distension, and failure to thrive. These symptoms are most commonly seen in children between 6 and 24 months of age. Atypical celiac disease is characterized by milder gastrointestinal symptoms. It is associated with extra-intestinal manifestations, such as iron deficiency anemia, osteoporosis, short stature, arthritis, infertility, peripheral neuropathy, hypertransaminasemia, and, in some cases, liver failure at the time of diagnosis. Latent celiac disease applies to patients who carry HLA-DQ2 and/or HLA-DQ8, with or without positive serology, and who have not yet developed villous atrophy but may have mild inflammation or immune activation. Patients in this subset may be asymptomatic or may have extra-intestinal manifestations. Silent celiac disease is characterized by positive serology and villous atrophy in an otherwise asymptomatic patient. After undertaking a gluten-free diet some asymptomatic patients will notice improvement in different physical and psychological aspects of their life, such as improved appetite, reduced fatigue, or fewer behavioral abnormalities. Regardless of the subtype, many celiac disease cases go undiagnosed, which exposes patients to the risk of long-term complications, for example, infertility and malignancies, e.g., lymphoma and intestinal carcinoma.

Presentation of celiac disease can vary widely. Celiac disease typically presents in children as a disease of failure to thrive associated with classic symptoms of malabsorption: predominately weight loss, steatorrhea, and multiple deficiencies, although other extra-intestinal symptoms, for example, failure of axial height development and delayed menarche in girls may be present.

Celiac disease prevalence is increased in at-risk conditions, such as a family history of celiac disease, autoimmune diseases, IgA deficiency, some genetic syndromes (Down syndrome, Turner syndrome and William syndromes) and especially type 1 diabetes and thyroiditis.

Genetic predisposition plays a significant role in celiac disease. Celiac disease is strongly associated with specific human leukocyte antigen (HLA) class II genes, HLA-DQ2 and HLA-DQ8, located on chromosome 6p21. Most celiac disease patients (approximately 95%) express genes encoding the major histocompatibility complex (MHC) class II protein HLA-DQ2. The remaining patients are usually HLA-DQ8-positive. The HLA-DQ2 haplotype is common and is carried by approximately 30% of Caucasian individuals, implying that the presence of HLA-DQ2 and/or HLA-DQ8 is necessary for disease development but not sufficient on its own as its estimated risk effect is only 36% to 53%. Non-HLA genes also contribute to celiac disease predisposition.

Diagnosis of celiac disease typically relies on multiple criteria including: 1) presentation with typical celiac disease symptoms; 2) positivity of serological tests, including, for example, high titer IgA antibodies to tTG (anti-tTG), high titer antibodies to deamidated α-gliadin peptides; 3) HLA-DQ2 and/or HLA-DQ8 genotypes; 4) celiac enteropathy found on small bowel biopsy; and 5) response to a gluten-free diet. The wide variability of celiac disease presentation has prompted some clinicians to adopt a quantitative approach defined as the 'four out of five rule'. That is, the diagnosis of celiac disease is confirmed if at least four of the five criteria are fulfilled.

Dermatitis herpetiformis is a skin manifestation of celiac disease presenting with blistering rash and pathognomonic cutaneous IgA deposits. The predominant symptoms are intense itching and burning. The rash has a characteristic symmetrical distribution. The elbows and upper forearms are affected in more than 90% of patients. Other sites commonly involved are the buttocks, knees, shoulders, sacrum, face, scalp, neck and trunk. Celiac-type villous atrophy in the upper small intestinal mucosa is found in 65% to 75% of patients with dermatitis herpetiformis. Even in patients with apparently normal biopsies, subtle changes in the mucosa, such as an increased number of intraepithelial lymphocytes, indicate gluten sensitization. Dermatitis herpetiformis patients may show the same array of manifestations, associated disorders and complications as in patients with celiac disease (autoimmune diseases, iron-deficient anemia, osteoporosis and malignancy). Dermatitis herpetiformis patients are generally put on a gluten-free diet because the rash of dermatitis herpetiformis is gluten sensitive.

Gluten ataxia has been defined as otherwise idiopathic sporadic ataxia with positive serological markers for gluten sensitization. Like celiac disease, it is an autoimmune disease characterized by damage to the cerebellum resulting in ataxia. Gluten ataxia patients typically have high titer anti-gliadin antibodies. Widespread deposition of transglutaminase antibodies has been found around brain vessels in patients with gluten ataxia. Gluten ataxia usually presents with pure cerebellar ataxia or, rarely, ataxia in combination with myoclonus, palatal tremor or opsoclonus myoclonus. Gluten ataxia is usually of insidious onset with a mean age at onset of 53 years. Many patients will have evidence of enteropathy on intestinal biopsy. Patients positive for anti-gliadin antibodies or anti-tTG antibodies with no alternative cause for their ataxia are typically put on a strict gluten-free diet with regular follow-up.

Gluten sensitivity, also referred to as non-celiac gluten sensitivity or gluten-intolerance, is generally characterized as a functional, morphological and immunological disorder that lacks all of the features of celiac disease, but nevertheless responds to gluten exclusion. Gluten sensitivity is distinct from celiac disease and is not accompanied by anti-tTG autoantibodies or other autoimmune comorbidities.

The small intestine of gluten sensitivity patients is typically normal. The symptoms of gluten sensitivity may resemble those associated with celiac disease but with a prevalence of extra-intestinal symptoms, such as behavioral changes, bone or joint pain, muscle cramps, leg numbness, weight loss and chronic fatigue. There are no laboratory biomarkers specific for gluten sensitivity. Usually the diagnosis is based on exclusion criteria; an elimination diet of gluten-containing foods followed by an open challenge is most often used to evaluate whether health improves with the elimination or reduction of gluten from the patient's diet.

Methods of Treatment

A subject is effectively treated whenever a clinically beneficial result ensues. This may mean, for example, a complete resolution of the symptoms associated with a gluten-related disorder, a decrease in the severity of the symptoms associated with a gluten-related disorder, or a slowing of the progression of symptoms associated with a gluten-related disorder. These methods can further include the steps of a) identifying a subject (e.g., a patient and, more specifically, a human patient) who has a gluten-related disorder; and b) providing to the subject a composition comprising L. paracasei CBA L74 or one or more L. paracasei CBA L74 metabolite described herein, such as any fermented food product or composition comprising L. paracasei CBA L74 in a physiologically acceptable carrier. An amount of such a composition provided to the subject that results in a complete resolution of the symptoms associated with a gluten-related disorder, a decrease in the severity of the symptoms associated with a gluten-related disorder, or a slowing of the progression of symptoms associated with a gluten-related disorder is considered a therapeutically effective amount. The present methods may also include a monitoring step to help optimize dosing and scheduling as well as predict outcome.

The methods disclosed herein can be applied to a wide range of species, e.g., humans, non-human primates (e.g., monkeys), horses, pigs, cows or other livestock, dogs, cats or other mammals kept as pets, rats, mice, or other laboratory animals. The compositions described herein are useful in therapeutic compositions and regimens or for the manufacture of a medicament for use in treatment of conditions as described herein (e.g., a gluten-related disorder.)

The compositions described herein can be administered orally as part of the ordinary daily diet of a subject. The food compositions may be administered as nutritional support to both children and adults. When formulated as pharmaceuticals, the compositions can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

Regardless of whether the compositions are formulated as food products or as pharmaceuticals, the dosage required will depend on the route of administration, the nature of the formulation, the nature of the subject's condition, e.g., immaturity of the immune system or a gastrointestinal disorder, the subject's size, weight, surface area, age, and sex, other drugs being administered, and the judgment of the attending clinicians. Suitable dosages are in the range of 0.01-1,000 mg/kg. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compound selected, formulation of the excipient, and its route of administration.

Effective doses can be extrapolated from dose-response curves derived from in vitro or animal model test systems. For example, analysis of effects on cell entry of gliadin peptides in cell-based assays can be useful. Compositions can also be assayed for effects on antibody responses, cytokine productions, and T-cell responses.

Wide variations in the needed dosage are to be expected in view of the spectrum of symptoms associated with gluten-related disorders, the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a composition can be administered once a week (for, for example, 4 weeks to many months or years); once a month (for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

Any method known to those in the art can be used to determine if a particular response is induced. Clinical methods that can assess the degree of a particular disease state can be used to determine if a response is induced. For example, a subject can be monitored for symptomatic relief, e.g., relief from diarrhea, abdominal pain, cramping, abdominal distention and ability to tolerate a gluten challenge. Alternatively or in addition, serum markers, imaging techniques, e.g., ultrasound, x-rays, and endoscopic methods can be used.

The compositions may also be administered in conjunction with other therapeutic modalities. These therapeutic modalities will vary according to the particular disorder, but can include, for example, dietary remedies, such as a gluten-free diet. In some embodiments, dietary remedies can include the introduction of wheat products from strains that have been engineered by selective breeding or recombinant technologies to express forms of gliadin that have reduced numbers of toxic T cell epitopes. In some embodiments, a dietary remedy can include administration of a prebiotic, i.e., an agent that stimulates the growth or activity of one of more species of intestinal flora that confer health benefits to the host. Exemplary prebiotics include trans-galactooligosaccharide, inulin, fructooligosaccharide and lactulose.

Other therapeutic modalities include administration of a therapeutic agent. A therapeutic agent can be an enzyme, for example an endopeptidase (also referred to as glutenase) that degrades gluten by targeting the proline-rich peptides that otherwise resist the body's natural proteases and contain highly immunogenic peptides. Exemplary endopeptidases include prolyl endopeptidases and ALV003, a combination of a cysteine endoprotease derived from germinating barley seeds and a prolyl endopeptidase from Sphingomonas capsulate.

Other therapeutic agents include inhibitors of the increased intestinal permeability typical of celiac disease, for example, AT-1001 (larazotide) an octapeptide inhibitor of paracellular permeability that inhibits gliadin-induced cytoskeleton rearrangement of intestinal epithelial cells, tight junction disassembly, and peak F-actin increment. Other therapeutic agents include tTG inhibitors, immune system modulators and desensitization therapy with peptide-based vaccines (Nevvax2).

Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Articles of Manufacture

The compositions described herein can also be assembled in kits, together with instructions for use. For example, the kits can include measured amounts of a composition including one or more food products fermented with *L. paracasei* CBA L74. The instructions for use can be conveyed by any suitable media. For example, they can be printed on a paper insert in one or more languages or supplied audibly or visually (e.g., on a compact disc). The packaging materials can include packaging materials, for example, vials, packets, containers. In some embodiments, the kits can include measured amounts of a composition comprising *L. paracasei* CBA L74 in a physiologically acceptable carrier along with packaging materials and instructions for use in any or the formats described above. In some embodiments, the kits can include measured amounts of a composition comprising one or more *L. paracasei* CBA L74 metabolites. In some embodiments the compositions can exclude *L. paracasei* CBA L74 cells, that is the metabolites can be partially or substantially separated from the *L. paracasei* CBA L74 cells. The components of the kit may be suitable for immediate use. The invention encompasses kits, however, that include concentrated formulations and/or materials that may require dilution prior to use.

EXAMPLES

Example 1: Materials and Methods

Peptides:

α-gliadin P31-P43 (SEQ ID NO.: 1) and P57-68 (SEQ ID NO.: 2) were synthesized in vitro and bound to the fluorochrome, lissamine, by Inbios, Naples, Italy. Chromatographic analyses indicated that the peptides were 99% pure.

Caco2 Peptide Entry Assay:

Cultures of Caco2 cells, a human epithelial colon carcinoma cell line, were incubated with the labeled peptides for 15 minutes. The labeled peptides were removed by repeated washing and the cells were examined under a confocal microscope. Morphological analysis showed that after 15 minutes of incubation, labeled peptides had entered the cells and localized to endocytotic vesicles, which appeared as small colored spots. Quantitative analysis was performed using a dedicated software package that evaluated the fluorescence intensity of multiple microscopic fields.

Caco2 Cell Culture:

CaCo-2 cells were grown in Dulbecco's Modified Eagle's Medium (DMEM) (GIBCO, San Giuliano Milanese, Italy), 10% fetal bovine serum (FBS) (GIBCO, San Giuliano Milanese, Italy) and 1 mM glutamine (GIBCO, San Giuliano Milanese, Italy), in an incubator at a temperature of 37° C. at a $CO_2$ concentration of 5%.

*L. paracasei* CBA L74 Culture:

*L. Paracasei* CBA L74 (International depository accession number LMG P-24778) was isolated as described in WO 2012/177556, which is herein incorporated by reference in its entirety. Cells were grown in 50 ml of DMEM supplemented with FBS and Glu, overnight at 37° C. at 160 oscillations per minute. The bacterial concentration was measured spectrophotometrically in a Beckman DU-7 spectrophotometer, at a wavelength of 600 nm. The Optical Density (OD) reading was used to calculate the bacterial concentration as follows: OD $2=1.5\times10^9$ cfu/ml. The different bacterial concentrations used for the experiments were obtained by diluting bacterial culture in fresh medium without antibiotic. For the experiments using supernatant alone, the bacterial culture was centrifuged at 3000 rpm for 10 minutes at room temperature. The supernatant was recovered and filtered through an 0.2 micron pore size filter.

Gliadin peptides and EGF-Alexa-488: Synthetic peptides (Inbios, 95% purity, MALDI-toff analysis as expected) were obtained by Ultrasart-D20 (Sartorius AG, Goettingen, Germany) filtration. The P31-43 peptide had the amino acid sequence: LGQQQPFPPQQPY (SEQ ID NO.: 1). The P57-68 peptide had the amino acid sequence: QLQPFPQPQLPY (SEQ ID NO.: 2). Peptides were conjugated with lissamine, a red fluorochrome excited by HeNe1 laser (543 nm) with 610 nm long band emission. EGF-Alexa-488 was obtained from Molecular Probes, San Giuliano Milanese, Italy.

Fluorescence Assay:

We tested the effect of *L. paracasei* CBA L74 on gliadin peptides or EGF-Alexa entrance in Caco-2 cells. Caco2 cells were grown on sterile glass coverslips, transferred into a 24-well plates and treated with different concentrations of *L. paracasei* CBA L74, in a range from $10^4$ to $10^8$ cfu/ml. For experiments using cell-free supernatant, Caco2 cells were treated with *L. paracasei* CBA L74, supernatant from collected from *L. paracasei* CBA L74 cultures that had reached a density of $10^8$ cfu/ml. The supernatant was used fresh or after exposure to heat. In some experiments, the supernatant was heated at 80° C. for 15 minutes. In other experiments, the supernatant was boiled for 5 minutes. Caco2 cells were treated with the different bacterial preparations in a 5% $CO_2$ atmosphere at 37° C., for 30 minutes and then incubated with gliadin peptides P31-43-lissamine (liss) or P57-68$^{liss}$ or with EGF-Alexa-488. Peptide concentrations were as follows: P31-43$^{liss}$, and P57-68$^{liss}$ at 20 micrograms/ml: unlabeled peptides were used at 50 micrograms/ml; EGF-Alexa-488 at 10 micrograms/ml. After the addition of the peptides, the cells were incubated in 5% $CO_2$ atmosphere at 37° C. for 30 minutes. The medium was then removed by three washes with PBS 1× (Gibco). Coverslips were briefly fixed (5 minutes) with paraformaldehyde 3% (Sigma-Aldrich) at room temperature, then mounted and observed by confocal microscope (LSM 510 Zeiss). Images were generated and analyzed with AIS Zeiss software to evaluate the intensity of fluorescence of the microscopic field under consideration. Magnification of the micrographs was the same for all the figures shown (63× objective). The labeled peptides and EGF-Alexa appeared in endocytosis vesicles that appear as small dots colored in red (peptides) or green (EGF).

Statistical Analysis:

Statistical analysis and graphics were obtained from GraphPad Prism. Mean and standard deviations were calculated. These were evaluated by Student's t test. Results having values of p<0.05 were considered significant.

Example 2: Effect of Live *L. Paracasei* CBA L74 on α-Gliadin Peptide Entry

Live *L. paracasei* CBA L74 reduced entry of both P31-43 and P57-68 into CaCo2 cells. Confocal fluorescence images are shown in FIG. 1. Control cells (left panels) that were incubated with lissamine labeled P31-43 in the absence of *L. paracasei* CBA L74, showed distinct patterns of fluorescence that corresponded to P31-43 containing endocytic vesicles (white arrows). In contrast, fluorescence was reduced in cells that were incubated with lissamine labeled P31-43 in the presence of *L. paracasei* CBA L74 (right panels).

Figure 2:
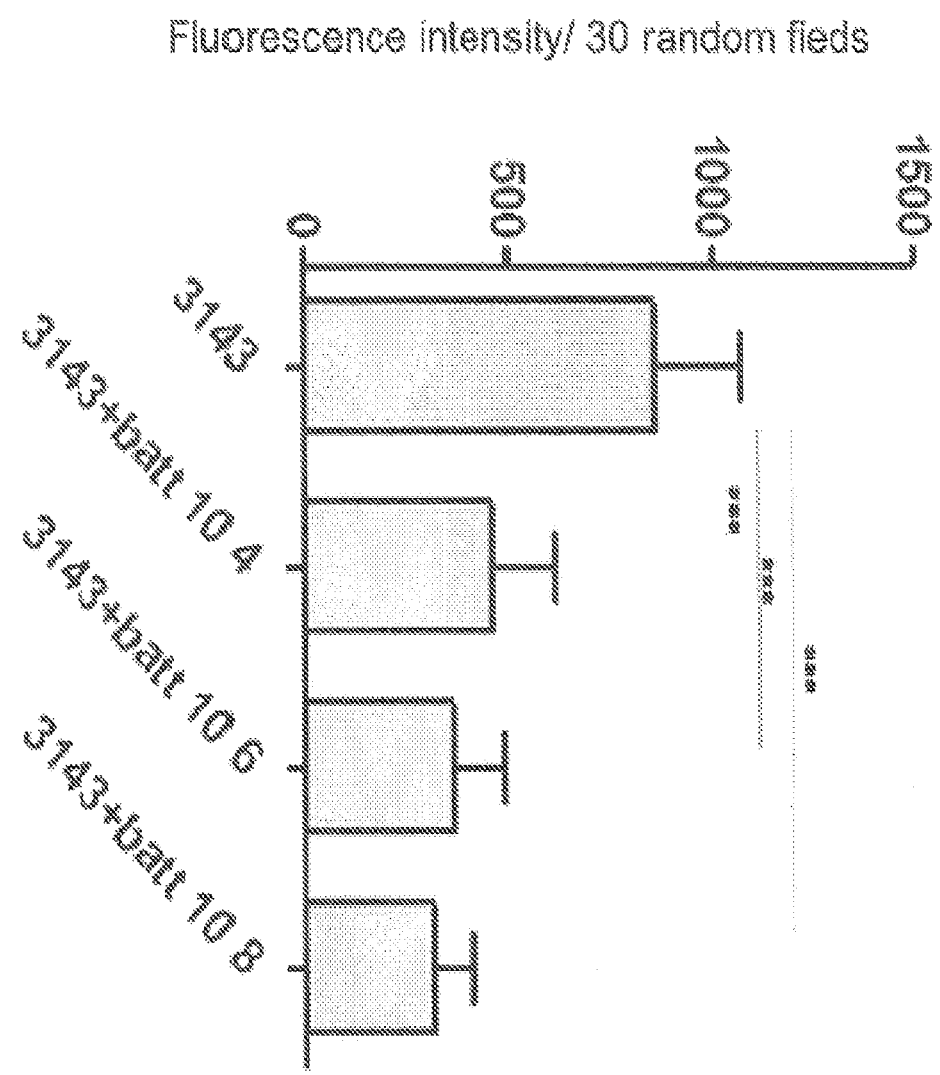
FIG. 2 is a graph depicting the results of an analysis of the effect of different concentrations of *Lactobacillus paracasei*, strain CBA L74 on entry of P31-43$^{liss}$ into CaCo2 cells.

Quantitative analysis indicated that the effect of *L. paracasei* CBA L74 on entry of P31-43 was dose-dependent and statistically significant. FIG. 2 shows the results of five independent experiments on duplicate samples. Fluorescence intensity was calculated for 30 random fields in each sample. As shown in FIG. 2, treatment of CaCo2 cells with $10^4$, $10^6$ and $10^8$ *L. paracasei* CBA L74, resulted in a statistically significant, dose-dependent decrease in P31-43 entry.

Figure 3:
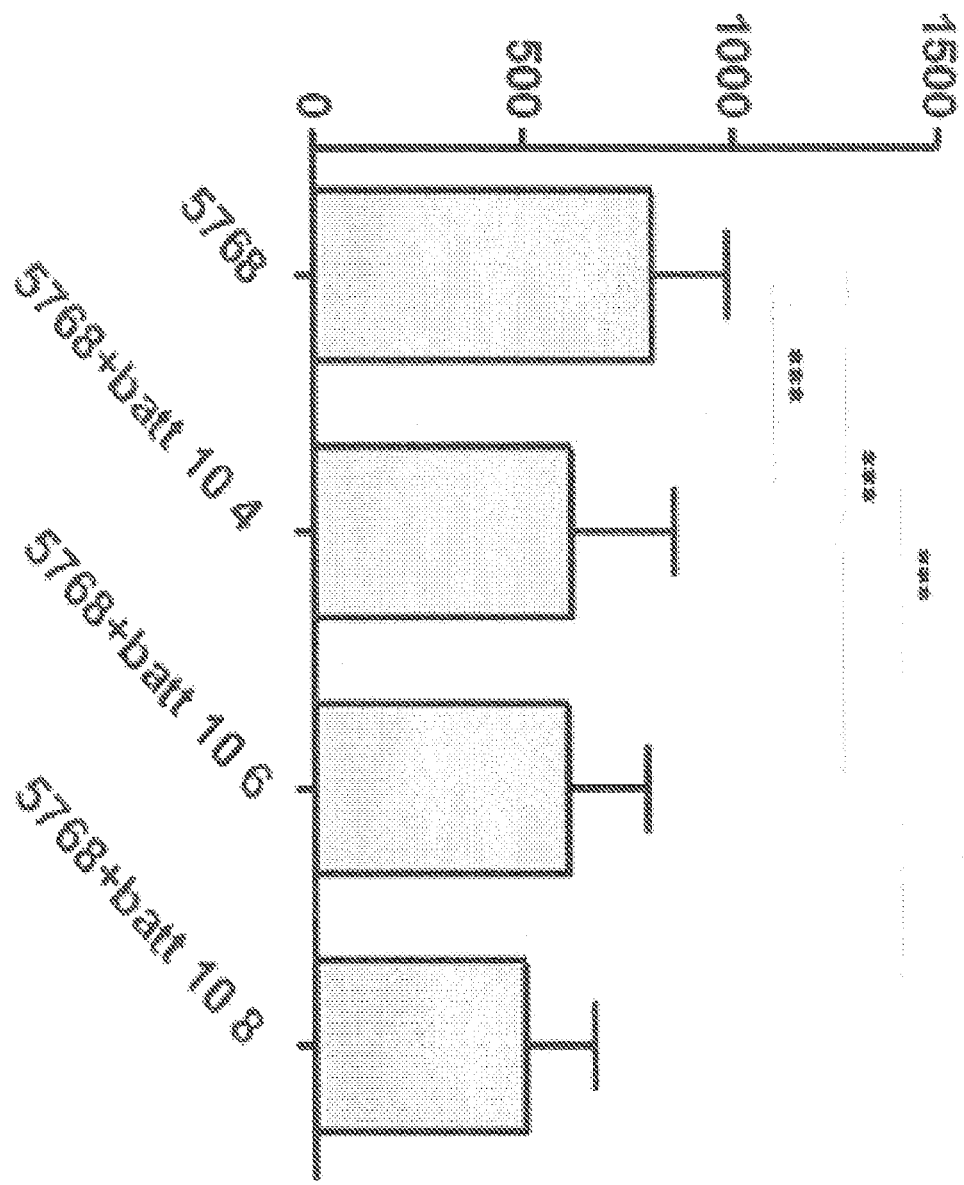
FIG. 3 is a graph depicting the results of an analysis of the effect of different concentrations of *Lactobacillus paracasei*, strain CBA L74 on entry of 57-68$^{liss}$ into CaCo2 cells.

A similar effect was observed for the P57-68 peptide. The experiment shown in FIG. 3 was performed exactly as the experiment of FIG. 2, except that P57-68 was used in place of P31-43. As shown in FIG. 3, treatment of CaCo2 cells with $10^4$, $10^6$ and $10^8$ *L. paracasei* CBA L74, resulted in a statistically significant, dose-dependent decrease in P57-68 entry.

Figure 4:
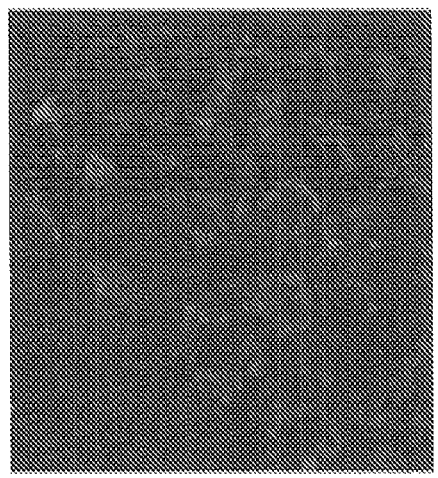
FIG. 4 is an analysis of the effect of *Lactobacillus paracasei*, strain CBA L74 DNA on entry of P31-43$^{liss}$ into CaCo2 cells.
Figure 4:
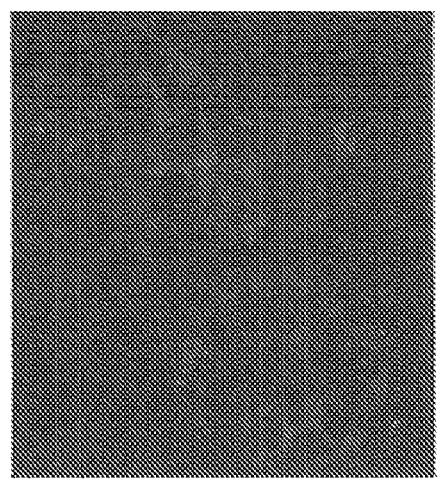

Example 3: Effect of *L. Paracasei* CBA L74 Isolated DNA on α-Gliadin Peptide Entry DNA from *L. paracasei* CBA L74 was extracted and purified by standard methods. As shown in FIG. 4, treatment of CaCo2 cells with P31-43 in the presence of an amount of *L. paracasei* CBA L74 DNA equivalent to that of $10^8$ cells, did not block peptide entry.

Example 4: Effect of *L. Paracasei* CBA L74 Culture Supernatant on α-Gliadin Peptide Entry

*L. paracasei* CBA L74 culture supernatant was collected by centrifugation and the culture supernatant was filtered to remove live bacteria and cell debris. Supernatant from the equivalent of $10^8$ cells was applied to CaCo2 cells in the presence of peptide P31-43. Control CaCO2 cells were treated with $10^8$ live *L. paracasei* CBA L74 cells. FIG. 5 shows the results of four independent experiments on duplicate samples. Fluorescence intensity was calculated for 30 random fields in each sample.

Figure 5A:
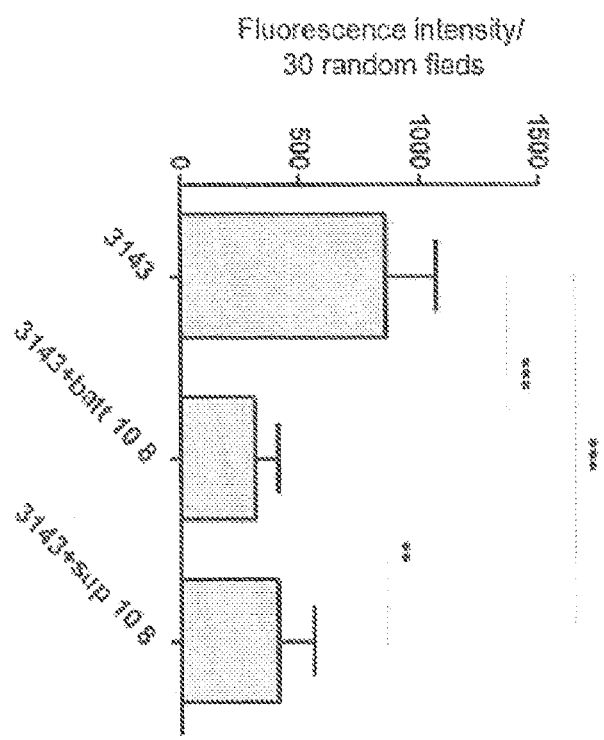
FIG. 5a is a graph depicting the results of an analysis of the effect of *Lactobacillus paracasei*, strain CBA L74 supernatant on entry of P31-43$^{liss}$ into CaCo2 cells.
Figure 5B:
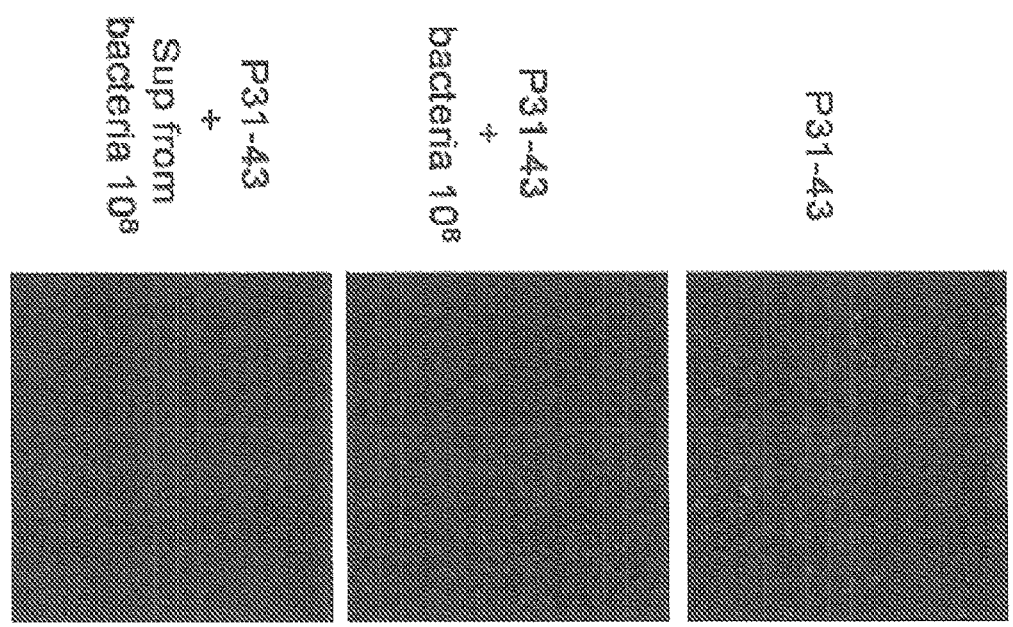
FIG. 5b is an analysis of the effect of *Lactobacillus paracasei*, strain CBA L74 supernatant on entry of P31-43$^{liss}$ into CaCo2 cells.

As depicted in the bar graph in FIG. 5a, treatment of CaCo2 cells with live *L. paracasei* CBA L74 cells again resulted in a statistically significant decrease in peptide P31-43 entry. Treatment of CaCo2 cells with *L. paracasei* CBA L74 culture supernatant resulted in a decrease of a similar magnitude. Confocal images for this experiment are shown in FIG. 5b. These images clearly show that *L. paracasei* CBA L74 culture supernatant reduced peptide P31-43 entry.

Figure 6A:
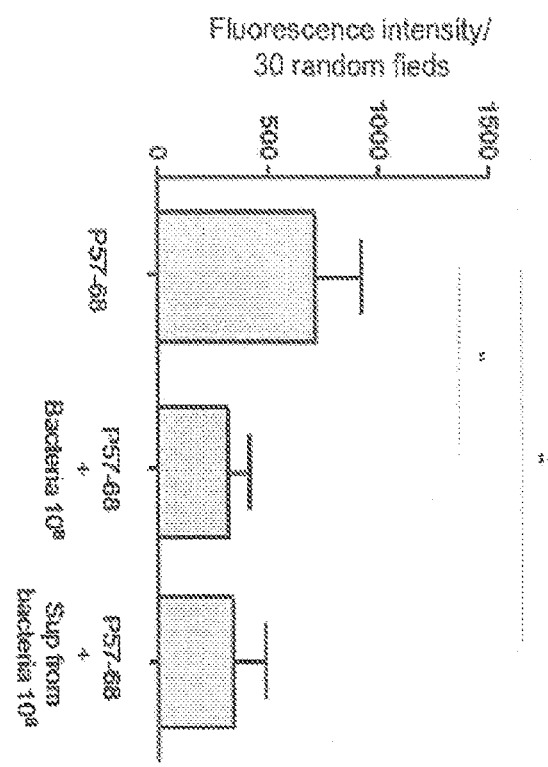
FIG. 6a is a graph depicting the results of an analysis of the effect of *Lactobacillus paracasei*, strain CBA L74 supernatant on entry of P57-68$^{liss}$ into CaCo2 cells.
Figure 6B:
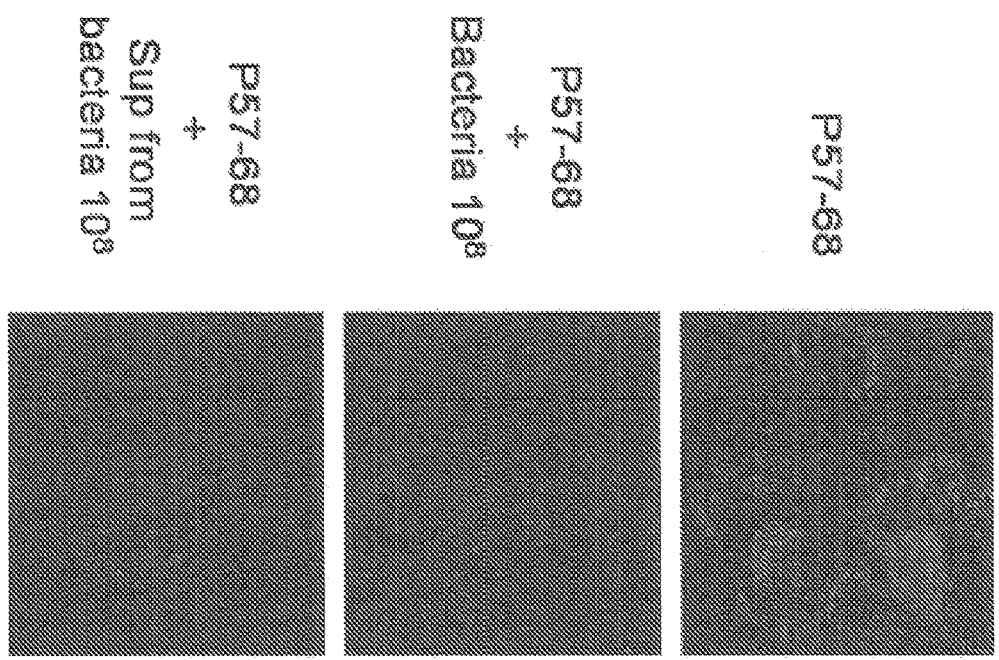
FIG. 6b is an analysis of the effect of *Lactobacillus paracasei*, strain CBA L74 supernatant on entry of P57-68$^{liss}$ into CaCo2 cells.

The results of a similar experiment in which P57-68 was substituted for P31-43 is shown in FIG. 6. Treatment of CaCo2 cells with live *L. paracasei* CBA L74 cells again resulted in a statistically significant decrease in peptide P57-68 entry (FIG. 6a). Treatment of CaCo2 cells with a *L. paracasei* CBA L74 culture supernatant resulted in a decrease of a similar magnitude. Confocal images for this experiment are shown in FIG. 6b. These images clearly show that *L. paracasei* CBA L74 culture supernatant reduced peptide P57-68 entry.

Example 5: Effect of Heat-Treated *L. Paracasei* CBA L74 Culture Supernatant on α-Gliadin Peptide Entry

Figure 7A:
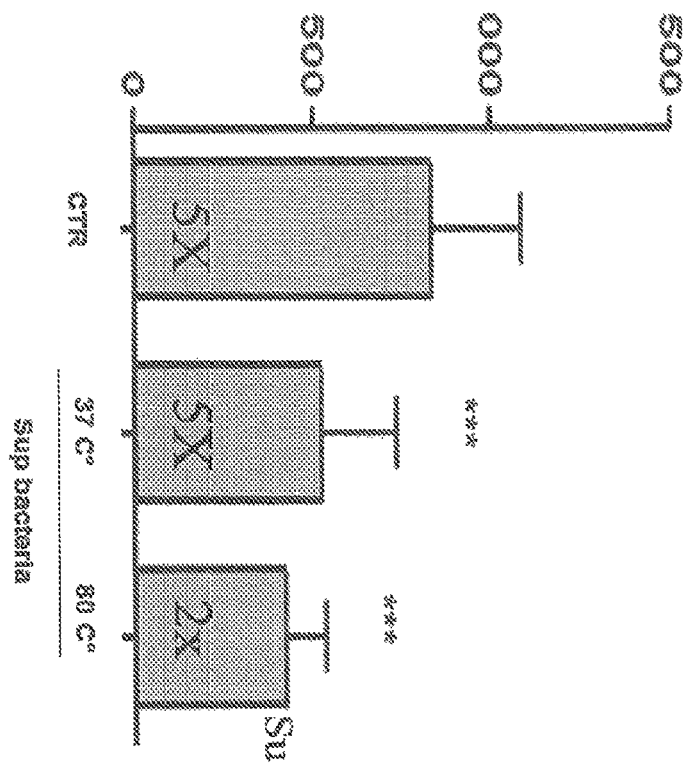
FIG. 7a is a graph depicting the results of an analysis of the effect of heat-treatment of *Lactobacillus paracasei*, strain CBA L74 supernatant on entry of P31-43$^{liss}$ into CaCo2 cells.
Figure 7B:
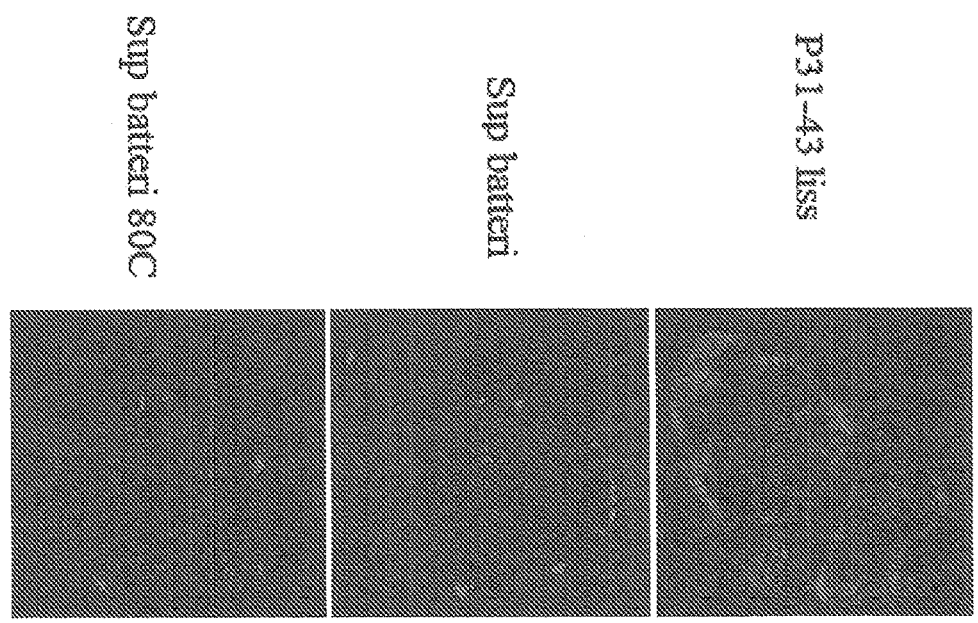
FIG. 7b is an analysis of the effect of heat-treatment of *Lactobacillus paracasei*, strain CBA L74 supernatant on entry of P31-43$^{liss}$ into CaCo2 cells.

*L. paracasei* CBA L74 culture supernatant was collected according to the method of Example 4 and then heated for 30 minutes at either 37° or 80° C. for 30 minutes. The heated supernatants were then cooled and applied to Caco2 cells in the presence of P31-43. FIG. 7 shows the results of five independent experiments on duplicate samples for control cells that were not treated supernatant, five independent experiments on duplicate samples for control cells treated with unheated supernatant ("37° C.") and two independent experiments on duplicate samples for cells that had been treated with heated supernatant heated ("80° C."). Fluorescence intensity was calculated for 30 random fields in each sample. As shown in FIG. 7, supernatant heated to 80° C. retained the ability of unheated supernatant to block peptide P31-43 entry into CaCo2 cells. Confocal images for this experiment are shown in the right panel of FIG. 7. These images clearly show that heat-treated *L. paracasei* CBA L74 culture supernatant reduced peptide P31-43 entry to the same extent as did non-heat treated *L. paracasei* CBA L74 culture supernatant. Taken together, these data suggested that the effect of *L. paracasei* CBA L74 culture supernatant did not result from enzymatic activity.

Example 6: Effect of *L. Paracasei* CBA L74 Fermented Rice and Fermented Oats on α-Gliadin Peptide Entry

Figure 8:
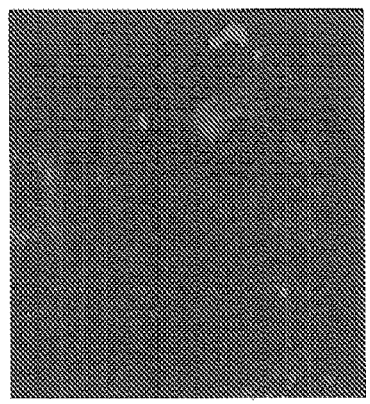
FIG. 8 is an analysis of the effect of *Lactobacillus paracasei*, strain CBA L74 supernatant from fermented rice on entry of P31-43$^{liss}$ into CaCo2 cells.
Figure 8:
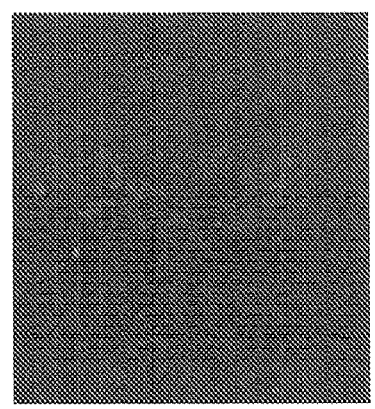
Figure 8:
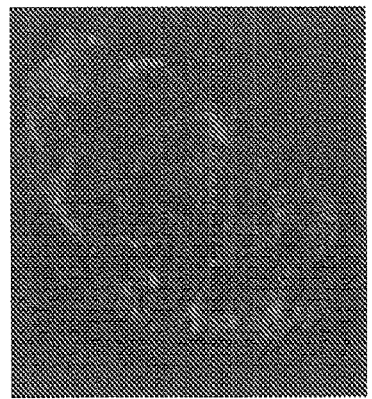
Figure 8:
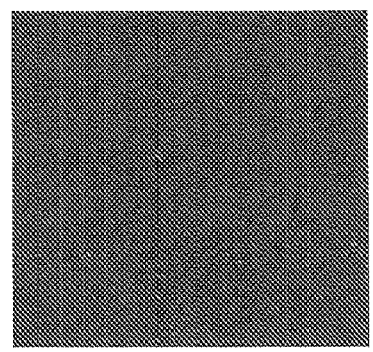
Figure 9:
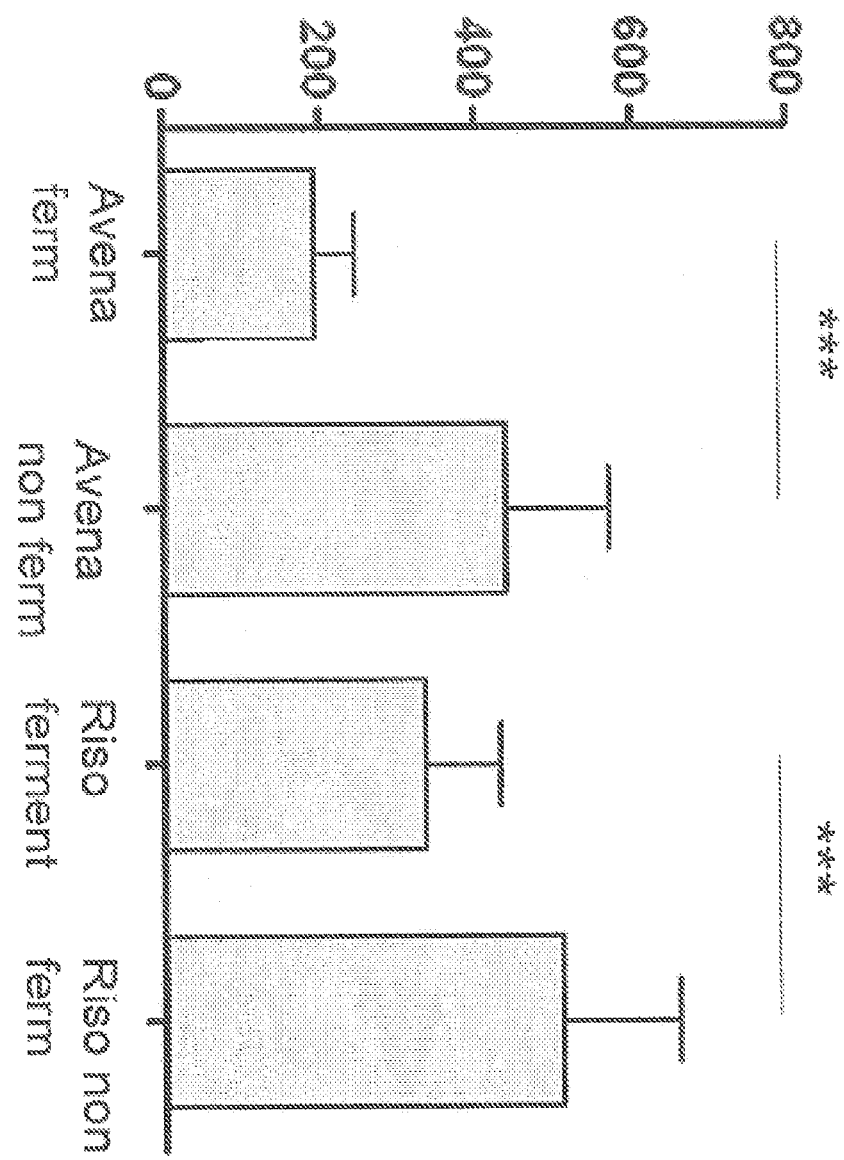
FIG. 9 is a graph depicting the results of an analysis of the effect of *Lactobacillus paracasei*, strain CBA L74 supernatant from fermented rice and fermented oats on entry of P31-43$^{liss}$ into CaCo2 cells.

*L. paracasei* CBA L74 fermented rice was prepared. Fermented rice, supernatant from the fermented rice, or heat-treated supernatant from the fermented rice was applied to CaCo2 cells in the presence of peptide P31-43 and peptide entry was monitored according to the method of Example 2. As shown in FIG. 8, all three treatments—fermented rice, supernatant from the fermented rice, or heat-treated supernatant from the fermented rice reduced peptide entry relative to untreated CaCo2 cells. As shown in FIG. 9, the reduction in peptide P31-43 entry in the presence of fermented rice was statistically significant (right-hand bars). A similar, statistically significant effect was observed in the presence of fermented oats (left hand bars).

Example 7: Effect of *L. Paracasei* CBA L74 Fermented Rice and Fermented Oats on Dextran-Texas Red Entry Into Caco2 Cells

Figure 10:
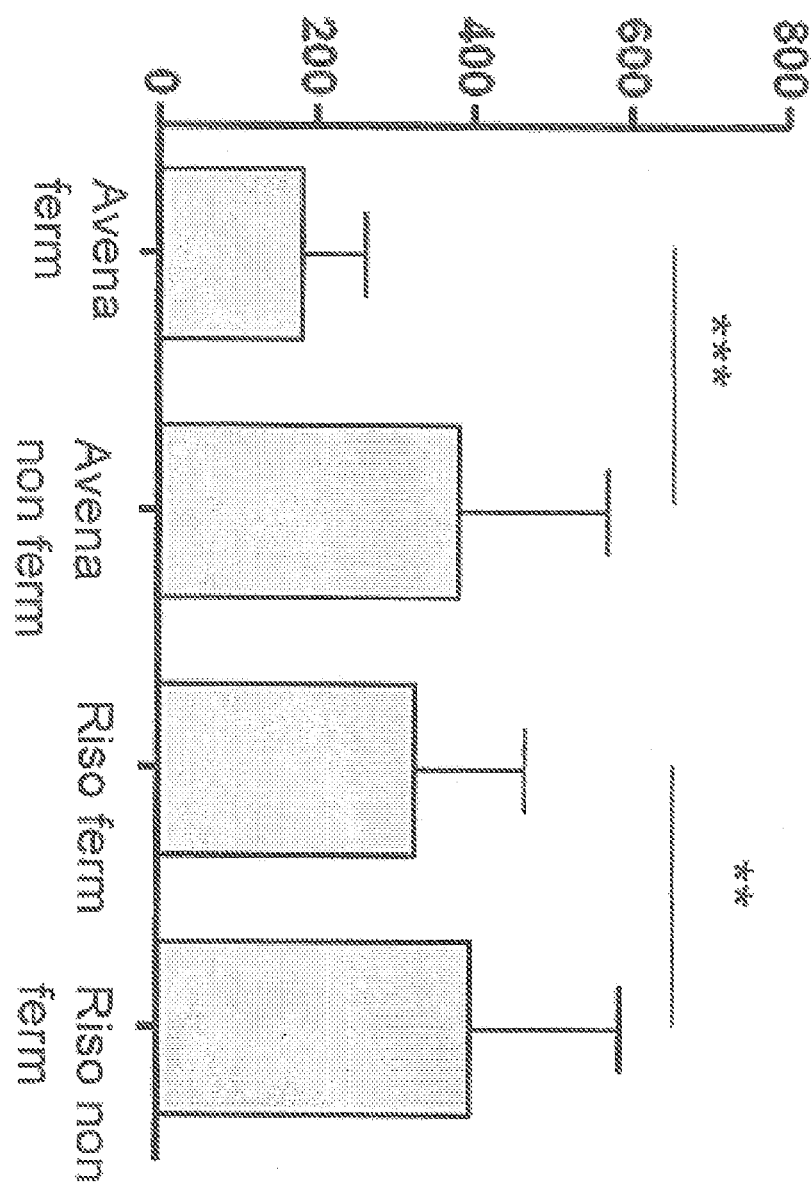
FIG. 10 is a graph depicting the results of an analysis of the effect of *Lactobacillus paracasei*, strain CBA L74 supernatant from fermented rice and fermented oats on entry of Dextran-Texas Red into CaCo2 cells.

*L. paracasei* CBA L74 fermented rice and fermented oats were prepared. As shown in FIG. 10, incubation of CaCo2 cells with either fermented rice or fermented oats resulted in a statistically significant reduction in cell entry of Dextran- Texas Red relative to cells that had been treated with unfermented rice or oats respectively. Since Dextran is generally taken up by cells via macropinocytosis, these data suggested that L. paracasei CBA L74 metabolites can block the macropinocytotic pathway.

Figure 11:
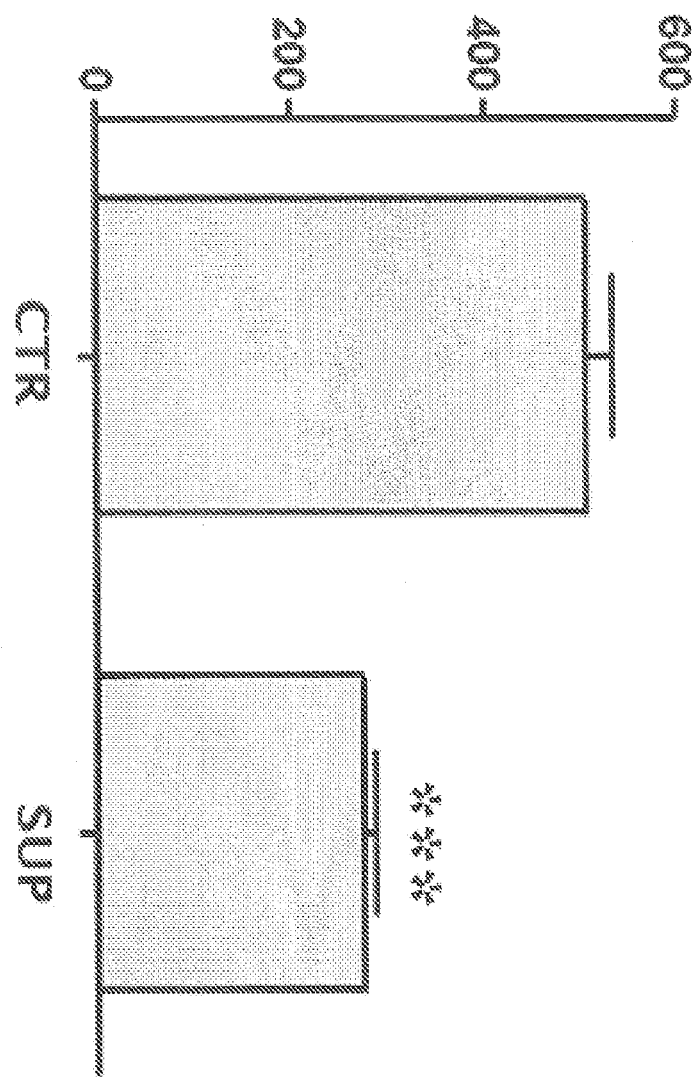
FIG. 11 is a graph depicting the results of an analysis of the effect of *Lactobacillus paracasei*, strain CBA L74 supernatant on entry of Alexa Fluor®-conjugated EGF into CaCo2 cells.
Figure 12:
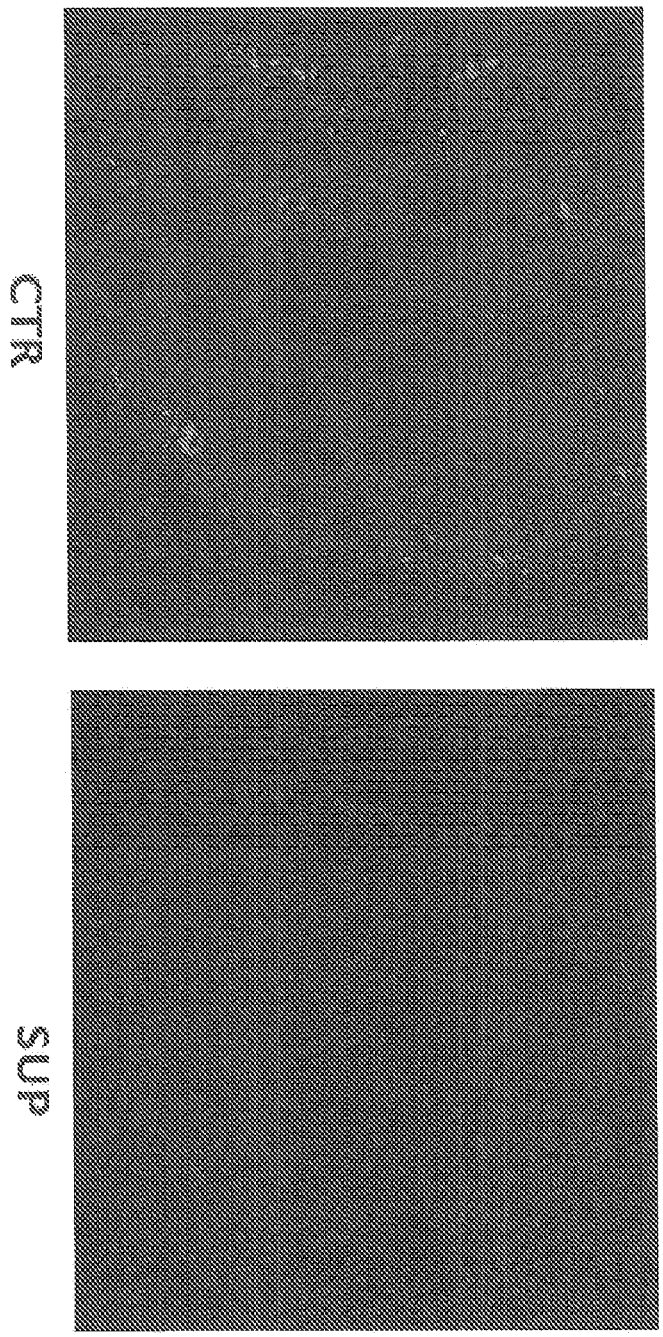
FIG. 12 is an analysis of the effect of *Lactobacillus paracasei*, strain CBA L74 supernatant on entry of Alexa Fluor®-conjugated EGF into CaCo2 cells.

Example 8: Effect of L. Paracasei CBA L74 Culture Supernatant on Epidermal Growth Factor (EGF) Entry into Caco2 Cells L. paracasei CBA L74 culture supernatant was collected according to the method of Example 4 and applied to Caco2 cells in the presence of Alexa Fluor®-conjugated EGF (Invitrogen). As depicted in the bar graph in FIG. 11, treatment of CaCo2 cells with L. paracasei CBA L74 culture supernatant resulted in a statistically significant decrease in cell entry of EGF. Confocal images for this experiment are shown in FIG. 12. Since EGF uptake requires specific receptor binding, e.g., to an EGF receptor, these data suggested that L. paracasei CBA L74 metabolites can block the clathrin-mediated endocytotic pathway.

Figure 13:
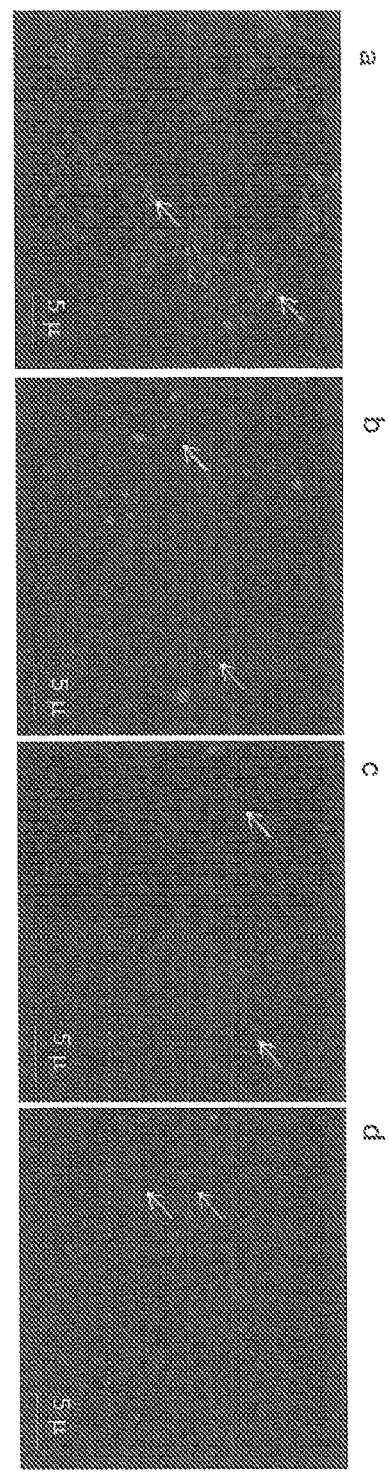
FIGS. 13a, 13b, 13c, and 13d are an analysis of the effect of *Lactobacillus paracasei*, strain CBA L74 on entry of P31-43$^{liss}$ into CaCo2 cells.
Figure 14:
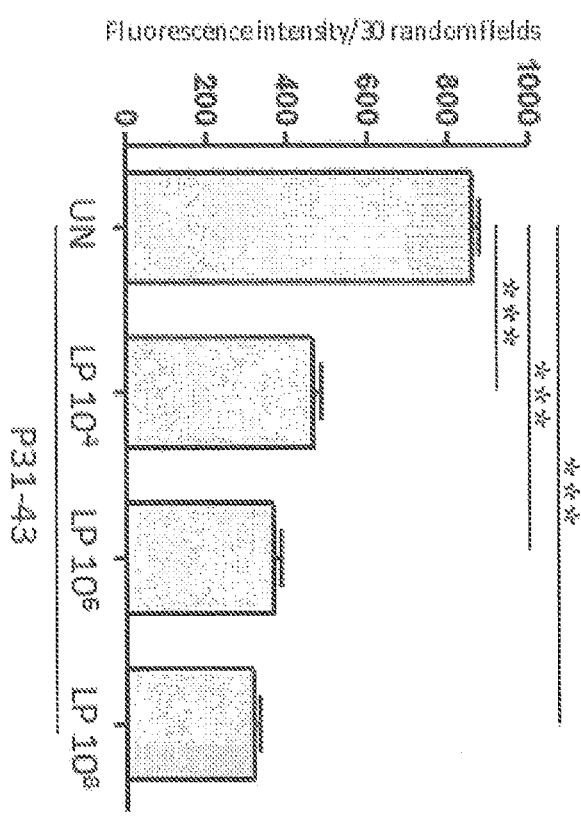
FIG. 14 is a graph depicting the results of an analysis of the effect of different concentrations of *Lactobacillus paracasei*, strain CBA L74 on entry of P31-43$^{liss}$ into CaCo2 cells.

Example 9: Concentration-Dependent Effect of L. paracasei CBA L74 on P31-43 and P57-68 Entry into Caco2 Cells Caco2 cells were treated with increasing concentrations of L. Paracasei CBA L74 and then incubated with gliadin peptides P31-43$^{liss}$ or P57-68$^{liss}$ as described in Example 1. Endocytosis vesicles that contained labeled P31-43 or labeled P57-68 appeared as red spots with a cytosolic distribution after 30 minutes of exposure. L. paracasei CBA L74 treatment resulted in a dose-dependent reduction in both P31-43 and P57-68 entry into Caco-2 cells. As shown in FIGS. 13b, 13c, and 13d, for P31-43, treatment with $10^4$, $10^6$ and $10^8$ cfu/ml of L. paracasei CBA L74, respectively resulted in a reduction of fluorescence intensity relative to that seen in untreated control cells (FIG. 13a). White arrows indicate vesicles containing P31-43$^{liss}$. These results are presented quantitatively in FIG. 14. Fluorescence intensity was calculated for 30 random fields for each sample. The data in FIG. 14 were representative of five independent experiments. The bar graph in FIG. 14 compares fluorescence intensity for untreated control cells ("UN") with that of cells that were exposed to P31-43$^{liss}$ in the presence of $10^4$, $10^6$ or $10^8$ cfu/ml of L. paracasei CBA L74 cells. Treatment with L. paracasei CBA L74 resulted in a statistically significant decrease in fluorescence intensity of 50%, 70% and 75%, respectively for $10^4$, $10^6$ or $10^8$ cfu/ml of L. paracasei CBA L74 cells (***=p<0.001).

Figure 15:
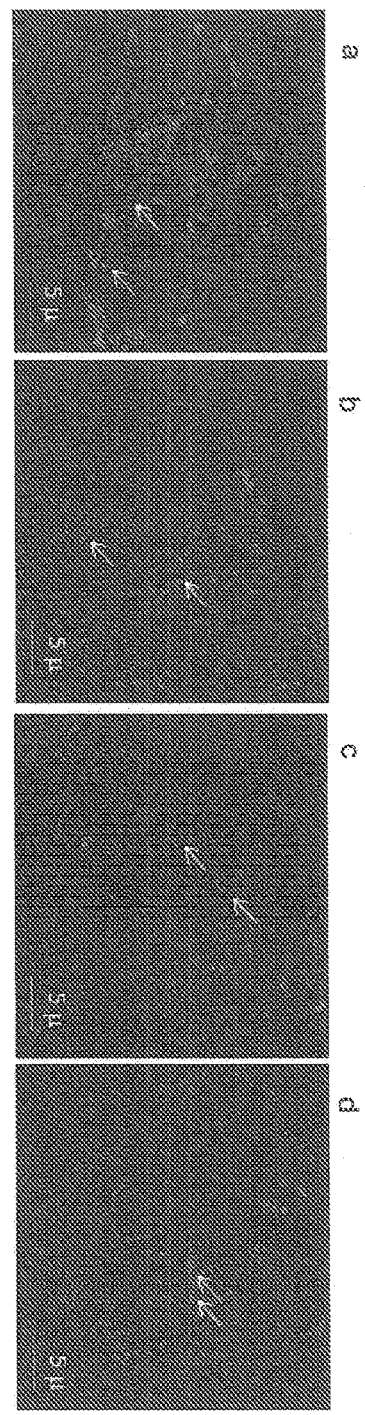
FIGS. 15a, 15b, 15c, and 15d are an analysis of the effect of *Lactobacillus paracasei*, strain CBA L74 on entry of P57-68$^{liss}$ into CaCo2 cells.
Figure 16:
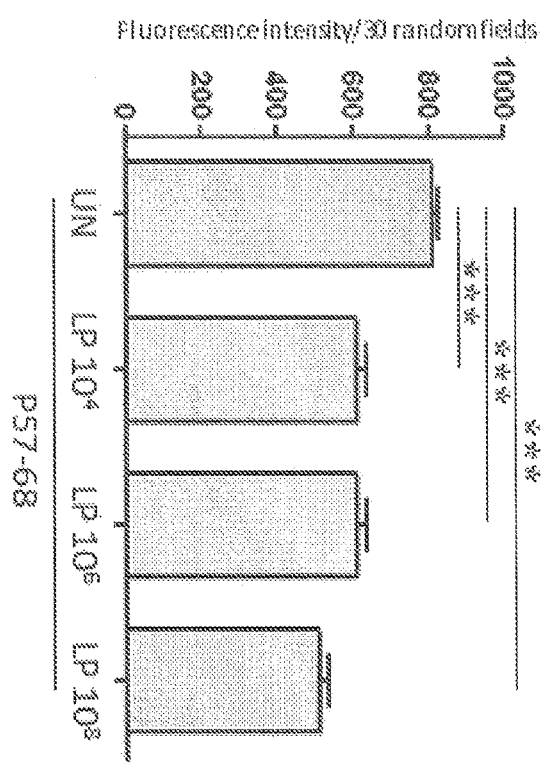
FIG. 16 is a graph depicting the results of an analysis of the effect of different concentrations of *Lactobacillus paracasei*, strain CBA L74 on entry of P57-68$^{liss}$ into CaCo2 cells.

As shown in FIGS. 15b, 15c, and 15d, for P57-68$^{liss}$, treatment with $10^4$, $10^6$ and $10^8$ cfu/ml of L. paracasei CBA L74, respectively resulted in a reduction of fluorescence intensity relative to that seen in untreated control cells (FIG. 15a). White arrows indicate vesicles containing P57-68$^{liss}$. These results are presented quantitatively in FIG. 16. Fluorescence intensity was calculated for 30 random fields for each sample. The data in FIG. 16 were representative of five independent experiments. The bar graph in FIG. 16 compares fluorescence intensity for untreated control cells ("UN") with that of cells that were exposed to P57-68$^{liss}$ in the presence of $10^4$, $10^6$ or $10^8$ cfu/ml of L. paracasei CBA L74 cells. Treatment with L. paracasei CBA L74 resulted in a statistically significant decrease in fluorescence intensity of 25%, 25% and 50%, respectively for $10^4$, $10^6$ or $10^8$ cfu/ml of L. paracasei CBA L74 cells. As shown in FIGS. 15B, 15C and 15D, for P57-68, treatment with $10^4$, $10^6$ and $10^8$ cfu/ml of L. paracasei CBA L74 resulted in a reduction of fluorescence intensity of 25%, 25% and 50%, respectively, relative to untreated control cells (***=p<0.001).

Figure 17:
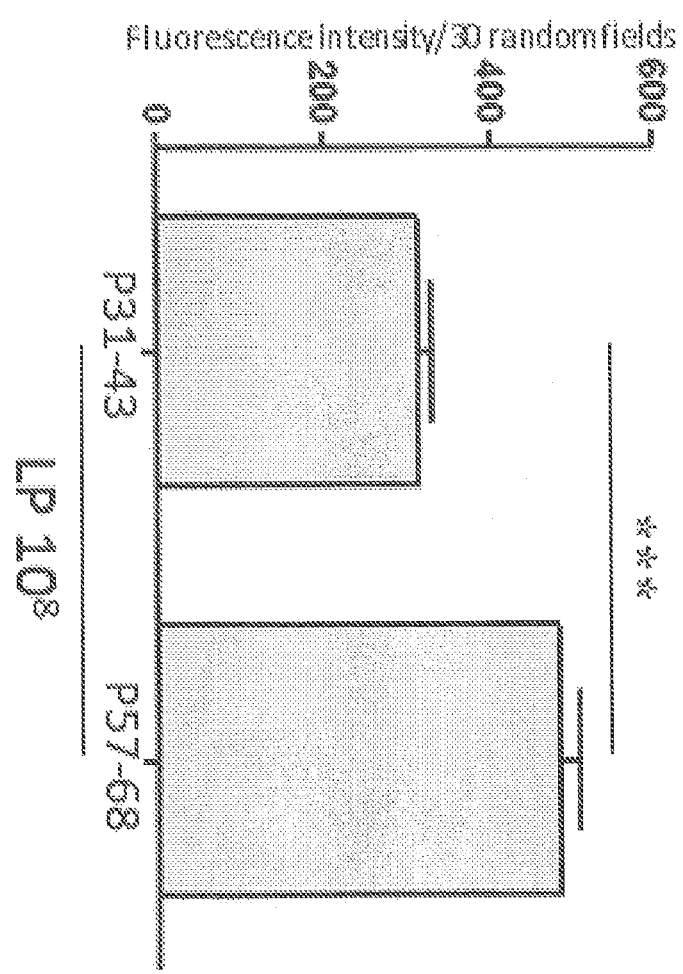
FIG. 17 is a graph depicting the results of an analysis of the effect of $10^8$ cfu/ml *Lactobacillus paracasei*, strain CBA L74 on entry of P31-43$^{liss}$ and P57-68$^{liss}$ into CaCo2 cells.

As shown in FIG. 17, treatment with $10^8$ cfu/ml of L. paracasei CBA L74 reduced fluorescence intensity by 75% for P31-43 and by 50% for P57-68. These data suggested that L. paracasei CBA L74 may be more efficient in reducing P41-43 entrance than in reducing P57-68 entrance, possibly reflecting different endocytotic pathways.

Figure 19:
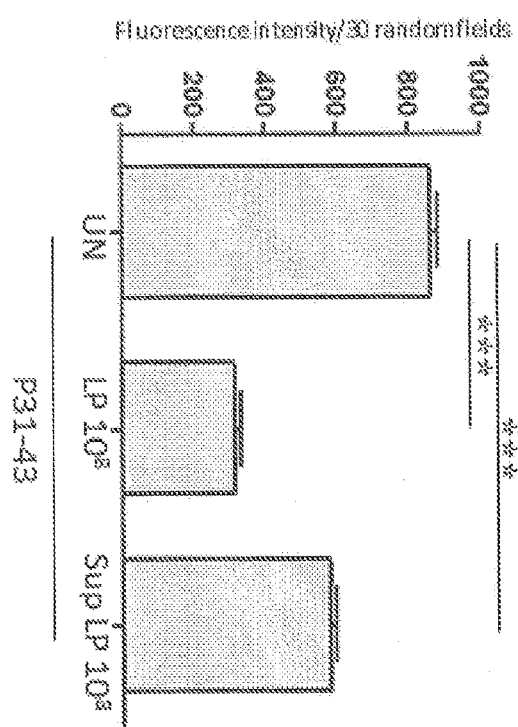
FIG. 19 is a graph depicting the results of an analysis of the effect of *L. paracasei*, strain CBA L74 cells and *L. paracasei*, strain CBA L74 supernatant on entry of P31-43$^{liss}$ into CaCo2 cells.
Figure 18:
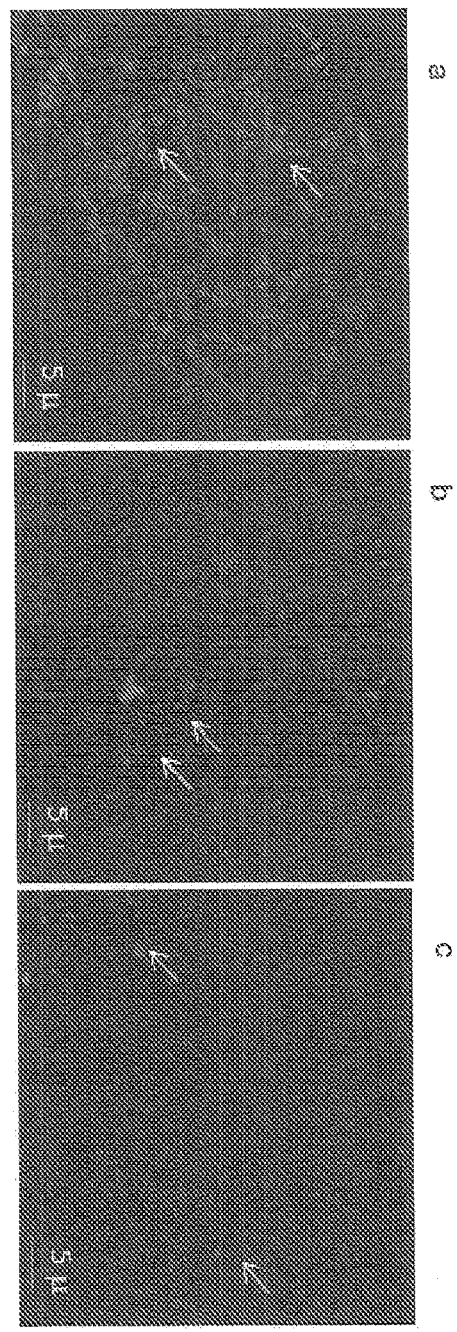
FIGS. 18a, 18b, and 18c are an analysis of the effect of *Lactobacillus paracasei*, strain CBA L74 supernatant on entry of P31-43$^{liss}$ into CaCo2 cells.

Example 10: Concentration-Dependent Effect of L. Paracasei CBA I74 Supernatant on P31-43 and P57-68 Entry into Caco2 Cells Caco2 cells were treated with L. paracasei CBA L74 supernatant or L. paracasei CBA L74 DNA as described in Example 1. The Caco2 cells were incubated for 30 minutes in supernatant or DNA from the equivalent of $10^8$ cfu/ml. As shown in FIGS. 18b and 18c, treatment with either L. paracasei CBA L74 cells or L. paracasei CBA L74 supernatant, respectively, resulted in a reduction in fluorescence intensity in cells exposed to P31-43$^{liss}$, relative to that seen in untreated control cells (FIG. 18a). These results are presented quantitatively in FIG. 19. Fluorescence intensity was calculated for 30 random fields for each sample. The data in FIG. 19 were representative of five independent experiments. The bar graph in FIG. 19 compares fluorescence intensity for untreated control cells ("UN") with that of cells that were exposed to P31-43$^{liss}$ in the presence of $10^8$ cfu/ml of L. paracasei CBA L74 cells ("LP $10^8$") or L. paracasei CBA L74 supernatant from a culture of $10^8$ cfu/ml L. paracasei CBA L74 ("Sup LP $10^8$"). As shown in FIG. 19, the L. paracasei CBA L74 supernatant significantly reduced P31-43 entry into Caco2 cells, calculated as reduction of fluorescence intensity, by about 25% relative to untreated control cells (***=p<0.001).

Figure 20:
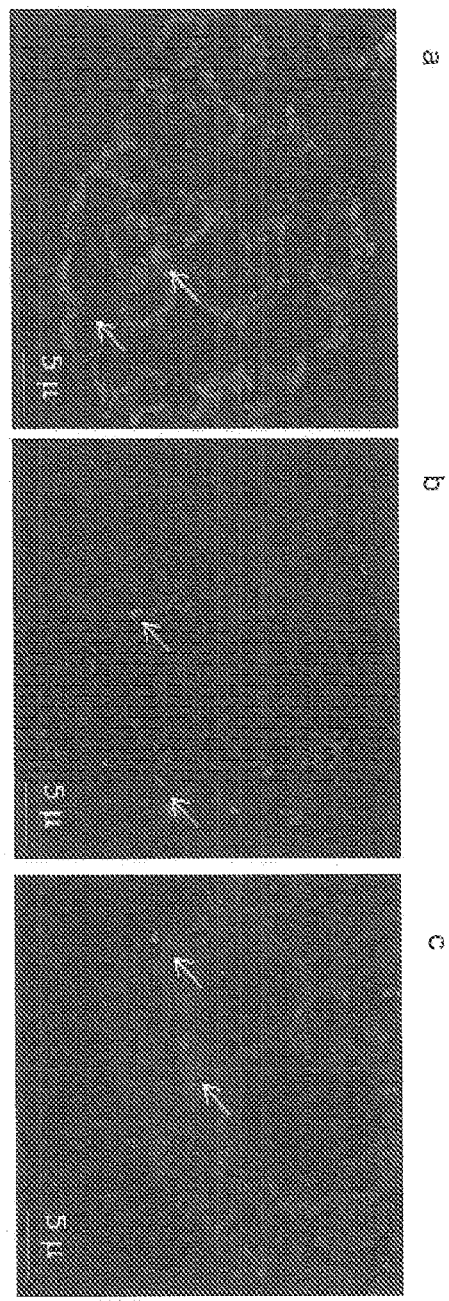
FIGS. 20a, 20b, and 20c are an analysis of the effect of *L. paracasei*, strain CBA L74 supernatant on entry of P57-68$^{liss}$ into CaCo2 cells.
Figure 21:
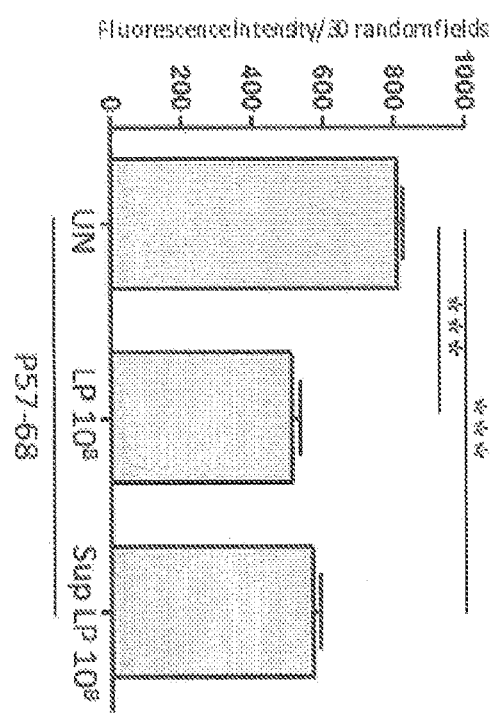
FIG. 21 is a graph depicting the results of an analysis of the effect of *L. paracasei*, strain CBA L74 cells and *L. paracasei*, strain CBA L74 supernatant on entry of P57-68$^{liss}$ into CaCo2 cells.

As shown in FIGS. 20b and 20c, treatment with either L. paracasei CBA L74 cells or L. paracasei CBA L74 supernatant, respectively, resulted in a reduction in fluorescence intensity in cells exposed to P57-68$^{liss}$, relative to that seen in untreated control cells (FIG. 20a). These results are presented quantitatively in FIG. 21. The bar graph in FIG. 21 compares fluorescence intensity for untreated control cells ("UN") with that of cells that were exposed to P57-68$^{liss}$ in the presence of $10^8$ cfu/ml of L. paracasei CBA L74 cells ("LP $10^8$") or L. paracasei CBA L74 supernatant ("Sup LP $10^8$") from a culture of $10^8$ cfu/ml L. paracasei CBA L74. As shown in FIG. 21, the L. paracasei CBA L74 supernatant significantly reduced P31-43 entry into Caco2 cells, calculated as reduction of fluorescence intensity, by about 40% relative to untreated control cells (***=p<0.001).

In contrast, treatment with purified DNA from L. paracasei CBA L74 had no effect on entry of P31-43 or P57-68 into Caco2 cells. Taken together, these data suggested that the metabolite responsible for reducing peptide entry may be secreted into the bacterial culture supernatant.

Figure 22:
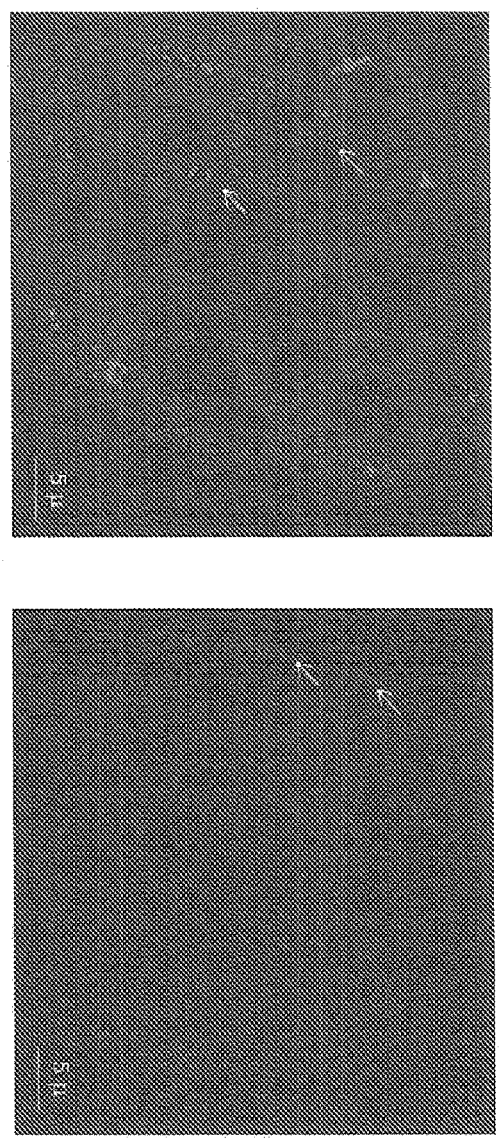
FIGS. 22a and 22b are an analysis of the effect of *L. paracasei*, strain CBA L74 supernatant on entry of EGF-Alexa 488 into Caco2 cells.
Figure 23:
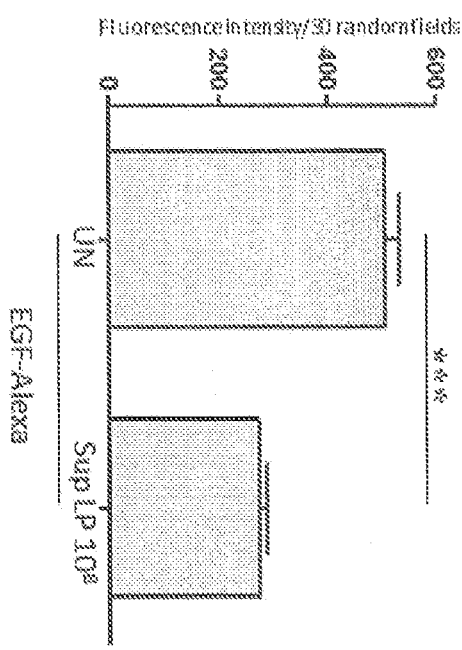
FIG. 23 is a graph depicting the results of an analysis of the effect of *L. paracasei*, strain CBA L74 supernatant on entry of EGF-Alexa 488 into Caco2 cells.

Example 11: Effect of L. Paracasei CBA L74 Supernatant on EGF-Alexa 488 Entry into Caco2 Cells Caco2 cells were treated with L. paracasei CBA L74 supernatant from a culture of $10^8$ cfu/ml L. paracasei CBA L74 followed by incubation with EGF-Alexa 488 for 30 minutes as described in Example 1. As shown in FIG. 22b, treatment with L. paracasei CBA L74 supernatant resulted in a reduction in fluorescence intensity in cells exposed to EGF-Alexa 488, relative to that seen in untreated control cells (FIG. 22a). These results are presented quantitatively in FIG. 23. Fluorescence intensity was calculated for 30 random fields for each sample. The data in FIG. 23 were representative of five independent experiments. The bar graph in FIG. 23 compares fluorescence intensity for untreated control cells ("UN") with that of cells that were exposed to EGF-Alexa 488 in the presence of L. paracasei CBA L74 supernatant ("Sup LP $10^8$"). As shown in FIG. 23, the L. paracasei CBA L74 supernatant significantly reduced EGF-Alexa 488 entry into Caco2 cells, calculated as reduction of fluorescence intensity, by about 50% relative to untreated control cells. The EGF-ALexa 488 entry appeared to be blocked at the cell membrane (***=p<0.001).

Figure 24:
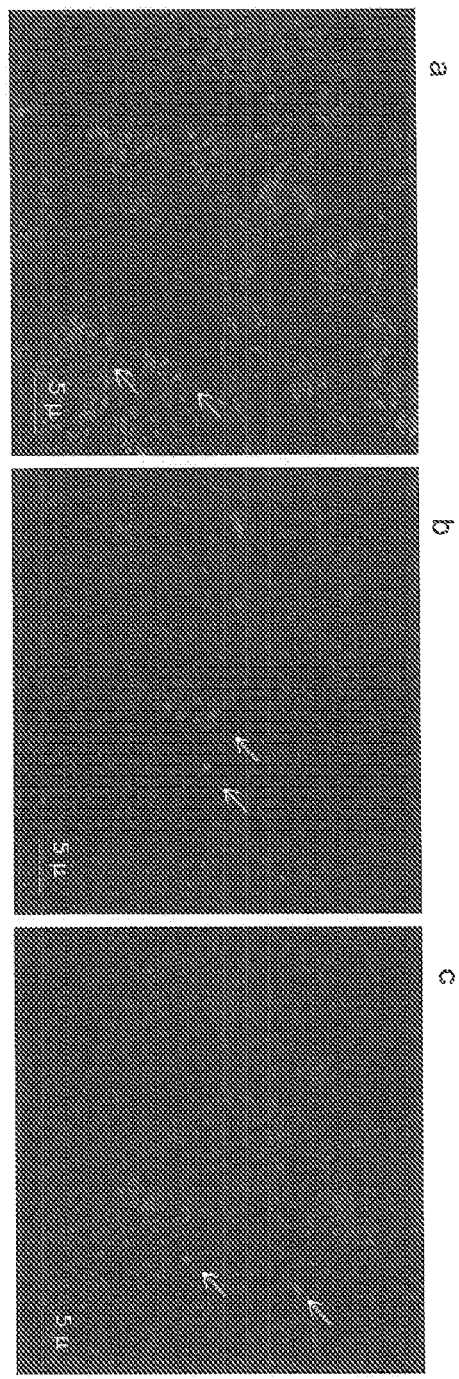
FIGS. 24a, 24b, and 24c are an analysis of the effect of removal of *L. paracasei*, strain CBA L74 supernatant on entry of P31-43$^{liss}$ into Caco2 cells.
Figure 25:
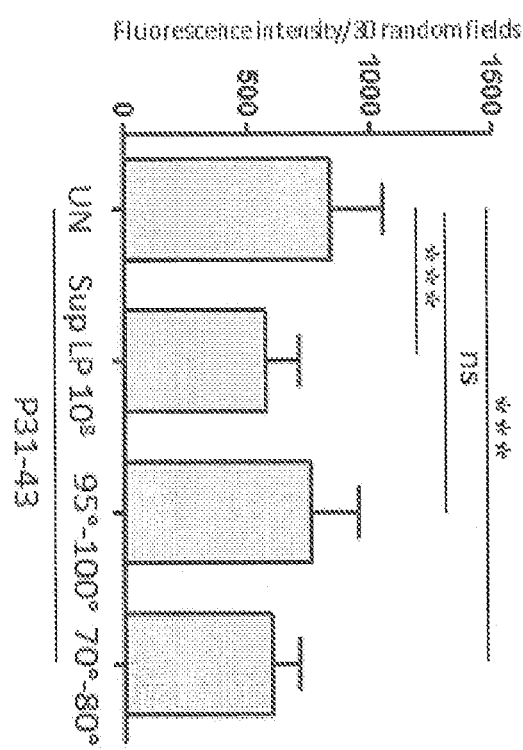
FIG. 25 is a graph depicting the results of an analysis of the effect of treatment and then removal of *L. paracasei*, strain CBA L74 supernatant on entry of P31-43$^{liss}$ into CaCo2 cells.

Example 12: Effect of L. Paracasei CBA L74 Supernatant on P31-43 Entry into Caco2 Cells Following Supernatant Removal Caco2 cells were incubated with L. paracasei CBA L74 supernatant from a culture of $10^8$ cfu/ml L. paracasei CBA L74 for 30 minutes as described in Example 1. The L. paracasei CBA L74 supernatant was then removed and replaced with DMEM. P31-43$^{liss}$ was added and peptide entry was monitored as described in Example 1. As shown in FIG. 24c, entry of P31-43-liss was significantly reduced, relative to untreated control cells (FIG. 24a) even after the L. paracasei CBA L74 supernatant had been removed and replaced with DMEM. FIG. 24b shows Caco2 cell that had been treated with L. paracasei CBA L74 supernatant that had not been removed. The bar graph in FIG. 25 compares fluorescence intensity for untreated control cells ("UN"); cells that were exposed to P31-43-liss in the presence of L. paracasei CBA L74 supernatant ("Sup LP 108") and cells that were exposed to P31-43-liss following removal of L. paracasei CBA L74 supernatant ("MEM") (***=p<0.001).

Figure 27:
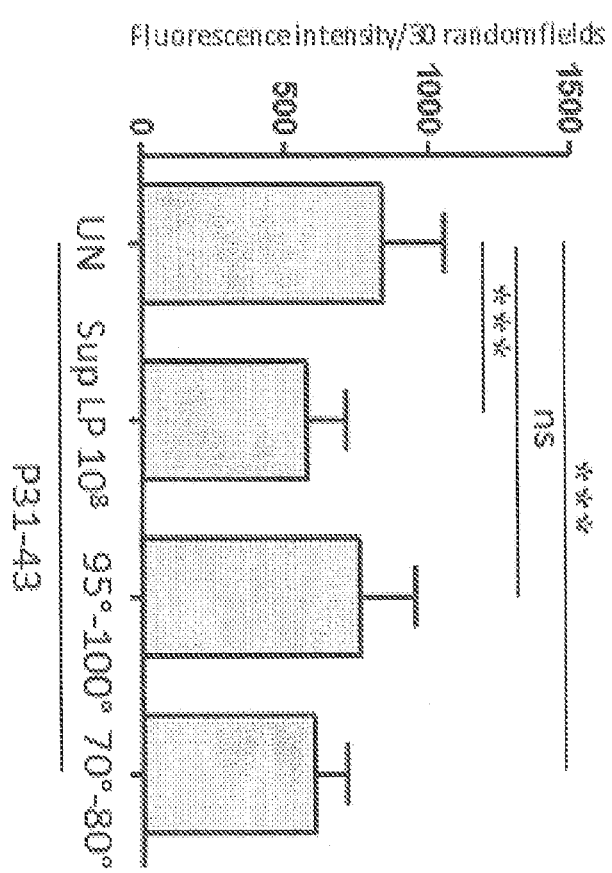
FIG. 27 is a graph depicting the results of an analysis of the effect of heat treatment of *L. paracasei*, strain CBA L74 supernatant on entry of P31-43$^{liss}$ into CaCo2 cells.
Figure 26:
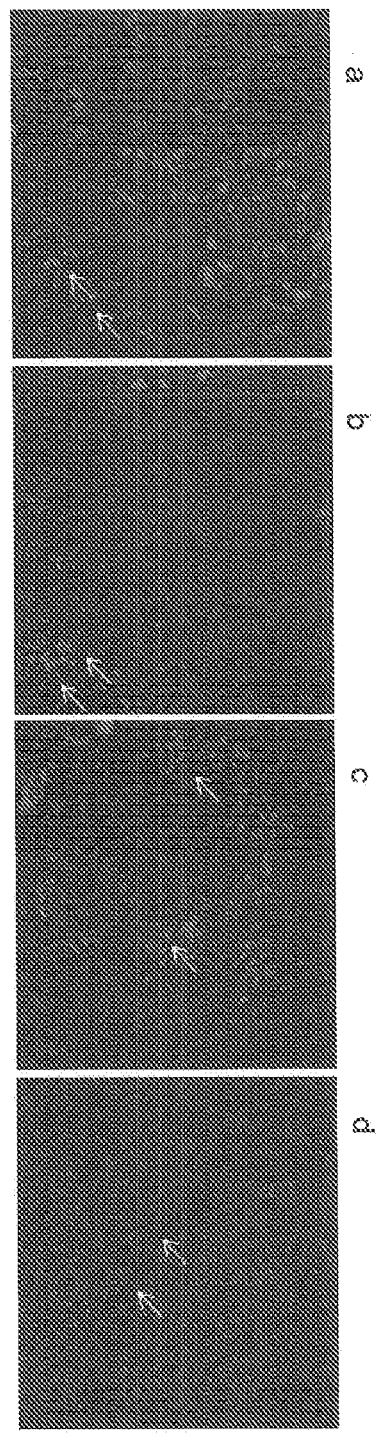
FIGS. 26a, 26b, 26c, and 26d are an analysis of the effect of heat treatment of *L. paracasei*, strain CBA L74 supernatant on entry of P31-43$^{liss}$ into Caco2 cells.

Example 13: Effect of Heat-Treated L. Paracasei CBA L74 Supernatant on P31-43 Entry into Caco2 Cells Caco2 cells were incubated with L. paracasei CBA L74 supernatant (from a culture of $10^8$ cfu/ml L. paracasei CBA L74) that had been heated treated by boiling for 5 minutes or by incubation at 80° C. for 15 minutes. P31-43-liss entry was assayed as described in Example 1. As shown in FIG. 26d, entry of P31-43-liss was reduced, relative to untreated control cells (FIG. 24a) even after the L. paracasei CBA L74 supernatant heated to 80° C. In contrast, entry of P31-43-liss not significantly reduced (FIG. 26c), relative to untreated control cells (FIG. 24a) when the L. paracasei CBA L74 supernatant had been heated at 95° C.-100° C. FIG. 26b shows Caco2 cell that had been treated with L. paracasei CBA L74 supernatant that had not been heat treated. The bar graph in FIG. 27 compares fluorescence intensity for untreated control cells ("UN"); cells that were exposed to P31-43-liss in the presence of L. paracasei CBA L74 supernatant ("Sup LP $10^8$") that had not been heat-treated; cells that were exposed to P31-43-liss in the presence of L. paracasei CBA L74 supernatant that had been boiled ("95°-100°"); and cells that were exposed to P31-43-liss in the presence of L. paracasei CBA L74 supernatant that had been heated at 80° C. ("70°-80°"). Taken together, these data suggested that the biological effector in the L. paracasei CBA L74 supernatant may not be an enzyme, since enzymatic activity is typically destroyed by temperatures of 80° C. (***=p<0.001).

What is claimed is:

1. A method of treating a subject having a gluten-related disorder, the method comprising:
    administering to the subject an effective amount of a composition comprising a probiotic bacterium Lactobacillus paracasei CBA L74, deposited at the Belgian Coordinated Collections of Micro-organisms (BCCM) Laboratorium voor Microbiologie (LMG) and having International Depository Accession Number LMG P-24778, wherein the probiotic bacterium reduces a symptom of gliadin peptide toxicity.

2. The method of claim 1, wherein the gliadin peptide is an α-gliadin peptide.

3. The method of claim 2, wherein the α-gliadin peptide has an amino acid sequence selected from the group consisting of LGQQQPFPPQQPY (SEQ ID NO: 1); QLQPFPQPQLPY (SEQ ID NO: 2); LGQQQPFPPQQPYPQPQPF (SEQ ID NO: 3); and LQLQPFPQPQLPYPQPQLPYPQPQLPYPQPQPF (SEQ ID NO: 4).

4. The method of claim 1, wherein the gluten-related disorder is celiac disease or gluten sensitivity.

5. The method of claim 1, wherein the symptom of gliadin peptide toxicity comprises at least one of inflammation, an autoimmune reaction, a gastrointestinal symptom, weight loss, anemia, osteoporosis, arthritis, infertility, peripheral neuropathy, and liver failure.

6. The method of claim 1, further comprising a step of administering a second treatment for the gluten-related disorder.

7. The method of claim 6, wherein the second treatment is a dietary or pharmaceutical therapy.

8. The method of claim 7, wherein the dietary therapy is a gluten-free diet.

9. The method of claim 1, wherein the probiotic bacterium Lactobacillus paracasei CBA L74, International Depository Accession Number LMG P-24778 is non-replicating.

10. The method of claim 9, wherein the probiotic bacterium Lactobacillus paracasei CBA L74, International Depository Accession Number LMG P-24778 is dead.

11. The method of claim 1, wherein the composition further comprises a food product or a pharmaceutical carrier.

12. A method of treating a subject having a gluten-related disorder, the method comprising:
    administering to the subject an effective amount of a composition comprising a fermented food product, wherein the fermented food product has been fermented by probiotic bacterium Lactobacillus paracasei CBA L74, deposited at the Belgian Coordinated Collections of Micro-organisms (BCCM) Laboratorium voor Microbiologie (LMG) and having International Depository Accession Number LMG P-24778, and the fermented food product reduces a symptom of gliadin peptide toxicity.

13. The method of claim 12, wherein the probiotic bacterium Lactobacillus paracasei CBA L74 in the composition is dead or has been rendered incapable of cell division.

14. The method of claim 12, wherein the food product is a dairy product or a cereal product.

15. The method of claim 12, wherein the composition further comprises a pharmaceutical carrier.

16. The method of claim 12, wherein the gliadin peptide is an α-gliadin peptide.

17. The method of claim 16, wherein the α-gliadin peptide has an amino acid sequence selected from the group consisting of LGQQQPFPPQQPY (SEQ ID NO: 1); QLQPFPQPQLPY (SEQ ID NO: 2); LGQQQPFP- PQQPYPQPQPF (SEQ ID NO: 3); and LQLQP-FPQPQLPYPQPQLPYPQPQLPYPQPQPF (SEQ ID NO: 4).

18. The method of claim 12, wherein the gluten-related disorder is celiac disease or gluten sensitivity.

19. The method of claim 12, wherein the symptom of gliadin peptide toxicity comprises at least one of inflammation, an autoimmune reaction, a gastrointestinal symptom, weight loss, anemia, osteoporosis, arthritis, infertility, peripheral neuropathy, and liver failure.

20. The method of claim 12, further comprising a step of administering a second treatment for the gluten-related disorder.

21. The method of claim 20, wherein the second treatment is a dietary or pharmaceutical therapy.

22. The method of claim 21, wherein the dietary therapy is a gluten-free diet.

23. A method of treating a subject having a gluten-related disorder, the method comprising:
administering to the subject an effective amount of a composition comprising a culture supernatant of probiotic bacterium *Lactobacillus paracasei* CBA L74, deposited at the Belgian Coordinated Collections of Micro-organisms (BCCM) Laboratorium voor Microbiologie (LMG) and having International Depository Accession Number LMG P-24778, wherein the culture supernatant reduces a symptom of gliadin peptide toxicity in a subject having a gluten-related disorder, and the culture supernatant comprises *Lactobacillus paracasei* CBA L74 cells and/or one or more sub-cellular bacterial components from *Lactobacillus paracasei* CBA L74 cells, wherein any *Lactobacillus paracasei* CBA L74 cells present in the culture supernatant are dead or have been rendered incapable of cell division.

24. The method of claim 23, wherein the composition further comprises a food product or a pharmaceutical carrier.

25. The method of claim 23, wherein the gliadin peptide is an α-gliadin peptide.

26. The method of claim 25, wherein the α-gliadin peptide has an amino acid sequence selected from the group consisting of LGQQQPFPPQQPY (SEQ ID NO: 1); QLQPFPQPQLPY (SEQ ID NO: 2); LGQQQPFPPQQPYPQPQPF (SEQ ID NO: 3); and LQLQP-FPQPQLPYPQPQLPYPQPQLPYPQPQPF (SEQ ID NO: 4).

27. The method of claim 23, wherein the gluten-related disorder is celiac disease or gluten sensitivity.

28. The method of claim 23, wherein the symptom of gliadin peptide toxicity comprises at least one of inflammation, an autoimmune reaction, a gastrointestinal symptom, weight loss, anemia, osteoporosis, arthritis, infertility, peripheral neuropathy, and liver failure.

29. The method of claim 23, further comprising administering a second treatment for the gluten-related disorder.

30. The method of claim 29, wherein the second treatment is a dietary or pharmaceutical therapy.

31. The method of claim 30, wherein the dietary therapy is a gluten-free diet.

\* \* \* \* \*